(12) United States Patent
Boronat et al.

(10) Patent No.: US 7,335,815 B2
(45) Date of Patent: *Feb. 26, 2008

(54) NUCLEIC ACID SEQUENCES TO PROTEINS INVOLVED IN ISOPRENOID SYNTHESIS

(75) Inventors: Albert Boronat, Barcelona (ES); Narciso Campos, Barcelona (ES); Ganesh M. Kishore, Creve Coeur, MO (US)

(73) Assignee: Calgene LLC, Davis, CA (US)

( * ) Notice: Subject to any disclaimer, the term of this patent is extended or adjusted under 35 U.S.C. 154(b) by 474 days.

This patent is subject to a terminal disclaimer.

(21) Appl. No.: 10/966,829

(22) Filed: Oct. 15, 2004

(65) Prior Publication Data

US 2005/0120406 A1 Jun. 2, 2005

Related U.S. Application Data

(63) Continuation of application No. 09/987,025, filed on Nov. 13, 2001, now Pat. No. 7,067,647, which is a continuation of application No. 09/549,787, filed on Apr. 14, 2000, now abandoned.

(60) Provisional application No. 60/129,899, filed on Apr. 15, 1999, provisional application No. 60/146,461, filed on Jul. 30, 1999.

(51) Int. Cl.
*C12N 15/29* (2006.01)
*C12N 15/61* (2006.01)
*C12N 15/82* (2006.01)
*A01H 5/10* (2006.01)

(52) U.S. Cl. .................. 800/298; 536/23.1; 536/23.2; 536/23.6; 435/320.1; 435/419

(58) Field of Classification Search .............. 800/278, 800/279, 282, 286, 289, 295, 298; 536/23.1, 536/23.2, 23.6; 435/183, 233, 320.1, 419, 435/468

See application file for complete search history.

(56) References Cited

U.S. PATENT DOCUMENTS

| | | | |
|---|---|---|---|
| 4,727,219 A | 2/1988 | Brar et al. | 800/266 |
| 5,304,478 A | 4/1994 | Bird et al. | 800/282 |
| 5,429,939 A | 7/1995 | Misawa et al. | 435/67 |
| 5,432,069 A | 7/1995 | Grüninger et al. | 435/183 |
| 5,545,816 A | 8/1996 | Ausich et al. | 800/298 |
| 5,618,988 A | 4/1997 | Hauptmann et al. | 800/282 |
| 5,684,238 A | 11/1997 | Ausich et al. | 800/298 |
| 5,693,507 A | 12/1997 | Daniell et al. | 435/470 |
| 5,750,865 A | 5/1998 | Bird et al. | 800/282 |
| 5,792,903 A | 8/1998 | Hirschberg et al. | 800/282 |
| 5,876,964 A | 3/1999 | Croteau et al. | 435/69.1 |
| 5,908,940 A | 6/1999 | Lane et al. | 549/413 |
| 6,281,017 B1 | 8/2001 | Croteau et al. | 435/468 |
| 6,303,365 B1 | 10/2001 | Martin et al. | 435/252.3 |
| 6,541,259 B1 | 4/2003 | Lassner et al. | 435/468 |
| 6,765,129 B1 | 7/2004 | Lichtenthaler et al. | 800/278 |
| 7,067,647 B2 * | 6/2006 | Boronat et al. | 536/23.6 |
| 2002/0069426 A1 | 6/2002 | Boronat et al. | 800/278 |
| 2002/0108148 A1 | 8/2002 | Boronat et al. | 800/284 |
| 2003/0148300 A1 | 8/2003 | Valentin et al. | 435/6 |
| 2003/0150015 A1 | 8/2003 | Norris et al. | 800/278 |
| 2003/0154513 A1 | 8/2003 | van Eenennaam et al. | 800/281 |
| 2003/0166205 A1 | 9/2003 | van Eenennaam et al. | 439/193 |
| 2003/0170833 A1 | 9/2003 | Lassner et al. | 435/125 |
| 2003/0176675 A1 | 9/2003 | Valentin et al. | 536/23.1 |
| 2003/0213017 A1 | 11/2003 | Valentin et al. | 800/287 |
| 2004/0018602 A1 | 1/2004 | Lassner et al. | 435/193 |
| 2004/0045051 A1 | 3/2004 | Norris et al. | 800/278 |

FOREIGN PATENT DOCUMENTS

| | | |
|---|---|---|
| CA | 2339519 | 2/2000 |
| CA | 2343919 | 3/2000 |
| CA | 2372332 | 11/2000 |
| DE | 198 35 219 | 8/1998 |
| EP | 0 531 639 | 3/1993 |
| EP | 0 674 000 | 9/1995 |
| EP | 0 723 017 | 7/1996 |
| EP | 0 763 542 | 3/1997 |
| EP | 1 033 405 | 9/2000 |
| EP | 1 063 297 | 12/2000 |
| FR | 2 778 527 | 11/1999 |
| GB | 560529 | 4/1944 |
| WO | WO 91/02059 | 2/1991 |
| WO | WO 91/09128 | 6/1991 |
| WO | WO 91/13078 | 9/1991 |
| WO | WO 93/18158 | 9/1993 |
| WO | WO 94/11516 | 5/1994 |
| WO | WO 94/12014 | 6/1994 |
| WO | WO 94/18337 | 8/1994 |
| WO | WO 95/08914 | 4/1995 |
| WO | WO 95/18220 | 7/1995 |
| WO | WO 95/23863 | 9/1995 |
| WO | WO 95/34668 | 12/1995 |
| WO | WO 96/02650 | 2/1996 |
| WO | WO 96/06172 | 2/1996 |
| WO | WO 96/13149 | 5/1996 |
| WO | WO 96/13159 | 5/1996 |
| WO | WO 96/36717 | 11/1996 |

(Continued)

OTHER PUBLICATIONS

Addlesee et al., "Cloning, sequencing and functional assignment of the chlorophyll biosyntheses gene, *chlP*, of synechocystis sp. PCC 6803," *FEBS Letters*, 389:126-130, 1996.

(Continued)

*Primary Examiner*—Russell P. Kallis
(74) *Attorney, Agent, or Firm*—Sonnenschein Nath & Rosenthal LLP

(57) ABSTRACT

Methods are provided for producing plants and seeds having altered isoprenoid content and compositions. The methods find particular use in increasing the isoprenoid levels in plants, and in providing desirable isoprenoid compositions in a host plant cell.

8 Claims, 2 Drawing Sheets

FOREIGN PATENT DOCUMENTS

| | | |
|---|---|---|
| WO | WO 96/38567 | 12/1996 |
| WO | WO 97/17447 | 5/1997 |
| WO | WO 97/27285 | 7/1997 |
| WO | WO 97/49816 | 12/1997 |
| WO | WO 98/04685 | 2/1998 |
| WO | WO 98/06862 | 2/1998 |
| WO | WO 98/18910 | 5/1998 |
| WO | WO 99/04021 | 1/1999 |
| WO | WO 99/04622 | 2/1999 |
| WO | WO 99/06580 | 2/1999 |
| WO | WO 99/07867 | 2/1999 |
| WO | 99/11757 | 3/1999 |
| WO | WO 99/19460 | 4/1999 |
| WO | WO 99/55889 | 11/1999 |
| WO | WO 99/58654 | 11/1999 |
| WO | WO 00/01650 | 1/2000 |
| WO | WO 00/08169 | 2/2000 |
| WO | WO 00/08187 | 2/2000 |
| WO | 00/17233 | 3/2000 |
| WO | WO 00/10380 | 3/2000 |
| WO | WO 00/11165 | 3/2000 |
| WO | WO 00/14207 | 3/2000 |
| WO | WO 00/22150 | 4/2000 |
| WO | WO 00/28005 | 5/2000 |
| WO | 00/34448 | 6/2000 |
| WO | WO 00/32757 | 6/2000 |
| WO | 00/42205 | 7/2000 |
| WO | 00/46346 | 8/2000 |
| WO | 00/63389 | 10/2000 |
| WO | WO 00/61771 | 10/2000 |
| WO | WO 00/63389 | 10/2000 |
| WO | WO 00/63391 | 10/2000 |
| WO | 00/65036 | 11/2000 |
| WO | WO 00/68393 | 11/2000 |
| WO | WO 01/04330 | 1/2001 |
| WO | WO 01/09341 | 2/2001 |
| WO | WO 01/12827 | 2/2001 |
| WO | WO 01/21650 | 3/2001 |
| WO | WO 01/44276 | 6/2001 |
| WO | WO 01/62781 | 8/2001 |
| WO | WO 01/79472 | 10/2001 |
| WO | WO 01/88169 | 11/2001 |
| WO | WO 02/00901 | 1/2002 |
| WO | WO 02/29022 | 4/2002 |
| WO | WO 02/31173 | 4/2002 |
| WO | WO 02/33060 | 4/2002 |
| WO | WO 02/46441 | 6/2002 |
| WO | 02/26933 | 7/2002 |
| WO | WO 02/072848 | 9/2002 |
| WO | WO 02/089561 | 11/2002 |
| WO | WO 03/034812 | 5/2003 |
| WO | WO 03/047547 | 6/2003 |

OTHER PUBLICATIONS

Alcala et al., Genbank Accession No. A1897027, Jul. 1999.
Arango et al., "Tocopherol synthesis from homogentisate in *Capsicum anuum* L. (yellow pepper) chromoplast membranes: evidence for tocopherol cyclase," *Biochem J.*, 336:531-533, 1998.
Arigoni et al., "Terpenoid biosynthesis from 1-deoxy-D-xylulose in higher plants by intramolecular skeletal rearrangement," *Proc. Natl. Acad. Sci. USA*, 94:10600-10605, 1997.
Baker et al, NCBI Association No. X64451, Dec. 1993.
Baker et al., "Sequence and characterization of the gcpE gene of *Escherichia coli*," *FEMS Microbiology Letters*, 94:175-180, 1992.
Bayley et al., "Engineering 2, 4-D resistance into cotton," *Theor. Appl. Genet.*, 83:645-649, 1992.
Bentley, "The shikimate pathway—A metabolic tree with many branches," *Critical Reviews Biochemistry and Molecular Biology*, 25(5):307-384, 1990.
Bevan et al., Accession T4 8445.
Bevan et al., Database EMBL, Accession No. AL035394, Feb. 1999.
Bevan et al., TREMBL Database Accession No. O65524, Aug. 1998.
Bevan, "Binary *agrobacterium* vectors for plant transformation," *Nucleic Acids Research*, 12:8711-8721, 1984.
Beyer et al., "Phytoene-forming activities in wild-type and transformed rice endosperm," *IRRN* 21(2-3):44-45, Aug.-Dec. 1996.
Bork et al, "Go hunting in sequence databases but watch out for the traps," *TIG*, 12(10):425-427, 1996.
Bouvier et al., "Dedicated roles of plastid transketolases during the early onset of isoprenoid biogenesis in pepper fruits," *Plant Physiol.*, 117:1423-1431, 1998.
Bowie et al., "Deciphering the message in protein sequences: tolerance to amino acid substitutions," *Science*, 247:1306-1310, 1990.
Bramley et al, "Biochemical characterization of transgenic tomato plants in which carotenoid synthesis has been inhibited through the expression of antisense RNA to pTOM5," *The Plant Journal*, 2(3):343-349, 1992.
Breitenbach et al., "Expression in *Eschenichia coli* and properties of the carotene ketolase from *Haematococcus pluvialis*," *FEMS microbiology Letters*, 140:241-246, 1996.
Broun et al., "Catalytic plasticity of fatty acid modification enzymes underlying chemical diversity of plant lipids," *Science*, 282:1315-1317, 1998.
Buckner et al., "The y[1] gene of maize codes for phytoene synthase," *Genetics*, 143(5):479-488, 1996.
Burkhardt et al., "Genetic engineering of provitamin A biosynthesis in rice endosperm," *Experientia*, 818-821.
Burkhardt et al., "Transgenic rice (*Oryza sativa*) endosperm expressing daffodil (*Narcissus pseudonarcissus*) phytoene synthase accumulates phytoene, a key intermediate of provitamin A biosynthesis," *The Plant Journal*, 11(5):1071-1078, 1997.
Cahoon et al., "Production of fatty acid components of meadowfoam oil in somatic soybean embryos," *Plant Physiology*, 124:243-251, 2000.
Campos et al., NCBI General Identifier BAA18485, Database EMBL, Accession No. AF148852, 2000.
Chaudhuri et al., "The purification of shikimate dehydrogenase from *Escherichia coli*," *Biochem. J.*, 226:217-223, 1985.
Chen et al., EMBL Sequence Database Accession No. AI995392, Sep. 1999.
Cheng et al. "Highly divergent methyltransferases catalyze a conserved reaction in tocopherol and plastoquinone synthesis in cyanobacteria and photosynthetic eukaryotes," *The Plant Cell*, 15:2343-2356, 2003.
Collakova et al., "Homogentisate phytyltransferase activity is limiting for tocopherol biosynthesis in arabiodopsis," *Plant Physiology*, 131(2):632-642, 2003.
Collakova et al., "Isolation and characterization of tocopherol prenyl transferase from synechocystic and arabidopsis," Poster Abstract, see REN-01-026.
Collakova et al., "Isolation and functional anlaysis of homogentisate phytyltransferase from synechocystis sp. PCC 6803 and arabidopsis," *Plant Physiology*, 127:1113-1124, 2001.
Cook et al., "Nuclear mutations affecting plastoquinone accumulation in maize," *Photosynthesis Research*, 31:99-111, 1992.
Cunillera et al., "Characterization of dehydrodolichyl diphosphate synthase of *Arabidopsis thaliana*, a key enzyme in dolichol biosynthesis," *FEBS Letters*, 477:170-174, 2000.
d'Amato et al., "Subcellular localization of chorismate-mutase isoenzymes in protoplasts from mesophyll and suspension-cultured cells of *Nicotiana silvestris*," *Planta*, 162:104-108, 1984.
d'Harlingue et al., "Plastid enzymes of terpenoid biosynthesis, purification and characterization of , tocopherol methyltransferase from capsicum chromoplasts," *The Journal of Biological Chemistry*, 260(28):15200-15203, 1985.
De Luca, "Molecular characterization of secondary metabolic pathways," *AgBiotech News and Information*, 5(6):225N-229N, 1993.
DEBEST ID:1262303, Database Accession No. AA586087, *Entrez Report*, 1997.
Desprez et al., Database EMBL, Accession No. Z34566, Jun. 1994.
Doerks et al., "Protein annotation: detective work for function prediction," *TIG*, 14:248-250, 1998.

Duncan et al., "The overexpression and complete amino acid sequence of *Escherichia coli* 3-dehydroquinase," *Biochem. J.*, 238:475-483, 1986.

Duvold et al., "Incorporation of 2-C-methyl-D-erythritol, a putative isoprenoid precursor in the mevalonate-independent pathway, into ubiquinone and menaquinone of *Escherichia coli*," *Tetrahedron Letters*, 38(35):6181-6184, 1997.

Eisenreich et al., "The deoxyxylulose phosphate pathways of terpenois biosynthesis in plants and microorganisms," *Chemistry & Biology*, 5(9):R221-R233, 1998.

Elliott, "A method for constructing single-copy *lac* fusions in *Salmonella typhimurium* and its application to the hemA-prfA operon," *Journal of Bacteriology*, 174:245-253, 1992.

Ericson et al., "Analysis of the promoter region of napin genes from *Brassica napus* demonstrates binding of nuclear protein in vitro to a conserved sequence motif," *Eur. J. Biochem.*, 197:741-746, 1991.

Estévez et al., "1-deoxy-D-xylulose-5-phosphate synthase, a limiting enzyme for plastidic isoprenoid biosynthesis in plants," *The Journal of Biological Chemistry*, 276(25):22901-22909, 2001.

Fedenko et al., Abstract: RU 2005353, Derwent Accession No. 1994-253787.

Fellermeier et al., "Cell-free conversion of 1-deoxy-D-xylulose 5-phosphate and 2-C-methyl-D-erythritol 4-phosphate into β-carotene in higher plants and its inhibition by fosmidomycin," *Tetrahedron Letters*, 40:2743-2746, 1999.

Fiedler et al., "The formation of homogentisate in the biosynthesis of tocopherol and plastoquinone in spinach chloroplasts," *Planta*, 155:511-515, 1982.

Fourgoux-Nicol et al., "Isolation of rapeseed genes expressed early and specifically during development of the male gametophyte," *Plant Molecular Biology*, 40:857-872, 1999.

Fraser et al., "Enzymic confirmation of reactions involved in routes to astaxanthin formation, elucidated using a direct substrate in vitro assay," *Eur. J. Biochem.*, 252:229-236, 1998.

Fraser et al., "In vitro characterization of astaxanthin biosynthetic enzymes," *The Journal of Biological Chemistry*, 272(10):6128-6135, 1997.

Fray et al., "Constitutive expression of a fruit phytoene synthase gene in transgenic tomatoes causes dwarfism by redirecting metabolites from the gibberellin pathway," *The Plant Journal*, 8(5):693-701, 1995.

Fray et al., "Identification and genetic analysis of normal and mutant phytoene synthase genes of tomato by sequencing, complementation and co-suppression," *Plant Molecular Biology*, 22:589-602, 1993.

Fuqua et al., "Characterization of melA: a gene encoding melanin biosynthesis from the marine bacterium *Shewanella colwelliana*," *Gene*, 109:131-136, 1991.

Furuya et al., "Production of tocopherols by cell culture of safflower," *Phytochemistry*, 26(10):2741-2747,1987.

Garcia et al., "Subcellular localization and purification of a p-hydroxyphenylpyruvate dioxygenase from cultured carrot cells and characterization of the corresponding cDNA," *Biochem. J.*, 325:761-769, 1997.

Gaubier et al., "A chlorophyll synthetase gene from *Arabidopsis thaliana*," *Mol. Gen. Genet.*, 249:58-64, 1995.

Gaubier et al., Database EMBL, Accession No. Q38833, Nov. 1996.

Goers et al., "Separation and characterization of two chorismate-mutase isoenzymes from *Nicotiana silvestris*," *Planta*, 162:109-116, 1984.

Grabse et al., "Loss of α-tocopherol in tobacco plants with decreased geranygeranyl reductase activity does not modify photosynthesis in optimal growth conditions but increases sensitivity to high-light stress," *Planta*, 213:620-628, 2001.

Harker et al., "Expression of prokaryotic 1-deoxy-D-xylulose-5-phosphatases in *Escherichia coli* increases carotenoid and ubiquinone biosynthesis," *FEB Letters*, 448:115-119, 1999.

Hecht et al., "Studies of the nonmevalonate pathway to terpenes: The role of the GcpE (IspG) protein," *PNAS*, 98(26):14837-14842, 2001.

Herrmann, "The shikimate pathway as an entry to aromatic secondary metabolism," *Plant Physiol.*, 107:7-12, 1995.

Herz et al., "Biosynthesis of terpenoids: YgbB protein converts 4-diphosphocytidyl-2C-methyl-D-erythritol 2-phosphate to 2C-methyl-D-erythritol 2, 4-cyclodiphosphate," *Proc. Natl. Acad. Sci. USA*, 97(6):2486-2490, 2000.

Kajiwara et al., "Isolation and functional identification of a novel cDNA for astaxanthin biosynthesis from *Haematococcus pluvialis*, and astaxanthin synthesis in *Escherichia coli*," *Plant Molecular Biology*, 29:343-352, 1995.

Kaneko et al, NCBI General Identifier No. 165372, Accession No. BAA18485, Jul. 2001.

Kaneko et al., "Complete genomic sequence of the filamentous nitrogen-fixing *cyanobacterium anabaena* sp. strain PCC 7120," *DNA Research*, 8(5):205-213, 2001.

Kaneko et al., Database EMBL, Accession No. P73726, Feb. 1997.

Kaneko et al., Database EMBL, Accession No. P73962, Jul. 1998.

Kaneko et al., EMBL Sequence Database Accession No. D90909, Oct. 1996.

Kaneko et al., NCBI General Identifier No. 1001725, Accession No. BAA10562, Feb. 2003.

Kaneko et al., TREMBL Database Accession No. P73727, Feb. 1997.

Keegstra., "Transport and routing of proteins into chloroplasts," *Cell*, 56(2):247-253, 1989.

Keller et al., "Metabolic compartmentaton of plastic prenyllipid biosynthesis evidence for the involvement of a multifunctional geranylgeranyl reductase," *Eur. J. Biochem*, 251:413-417, 1998.

Kishore et al., "Amino acid biosynthesis ihibitors as herbicides," *Ann. Rev. Biochem.*, 57:627-663, 1988.

Koziel et al., "Optimizing expression of transgenes with an emphasis on post-transcriptional events," *Plant Molecular Biology*, 32:393-405, 1996.

Kumagai et al., "Cytoplasmic inhibition of carotenoid biosynthesis with virus-derived RNA," *Proc. Nat'l Acad. Sci. USA*, 92:1679-1683, 1995.

Kuntz et al., "Identification of a cDNA for the plastid-located geranylgeranyl pyrophosphate synthase from capsicum annuum: correlative increase in enzyme activity and transcript level during fruit ripening," *the Plant Journal*, 2(1):25-34, 1992.

Lange et al., "A family of transketolases that directs isoprenoid biosynthesis via a mevalonate-independent pathway," *Proc. Natl. Acad. Sci. USA*, 95:2100-2104, 1998.

Lange et al., "Isoprenoid biosynthesis via a mevalonate-independent pathway in plants: cloning and heterologous expression of 1-deoxy-D-xylulose-5-phosphate reductoisomerase from peppermint," *Archives of Biochemistry and Biophysics*, 365(1):170-174, 1999.

Lange et al., "Mentha x piperita 1-deoxy-D-xylulose-5-phosphate reductoisomerase (DXR) mRNA," complete cds, Entrez Report, Accession No. AF116825, Apr. 1999.

Li et al., "Identification of a maize endosperm-specific cDNA encoding famesyl pyrophosphate synthetase," *Gene*, 171:193-196, 1996.

Lin et al., Database EMBL, Accession No. AC003672, Dec. 1997.

Lin et al., Database EMBL, Accession No. AC003673, Dec. 1997.

Lin et al., Database EMBL, Accession No. AC004077, Feb. 1998.

Linthorst et al., "Constitutive Expression of pathogenesis-related proteins PR-1, GRP, and PR-S in tobacco has no effect on virus infection," *The Plant Cell*, 1:285-291, 1989.

Lois et al., "Cloning and characterization of a gene from *escherichia coli* encoding a transketolase-like enzyme that catalyzes the synthesus of D-1-deoxyxylulose 5-phosphate, a common precursor for isoprenoid, thiamin, and pyridoxol biosynthesis," *Proc. Natl. Acad. Sci. USA*, 95(5):2105-2110, 1998.

Lopez et al., "Sequence of the bchG Gene from chloroflexus aurantiacus: relationship between chlorophyll synthase and other polyprenyltransferases," *Journal of Bacteriology*, 178(11):3369-3373, 1996.

Lotan et al., "Cloning and expression in *Escherichia coli* of the gene encoding β-C-4-oxygenase, that converts β-carotene to the Ketocarotenoid canthaxanthin in *Haematococcus pluvialis*," *FEBS Letters*, 364:125-128, 1995.

Mahmoud et al., "Metabolic engineering of essential oil yield and composition in mint by altering expression of deoxyxylulose phosphate reductoisomerase and menthofuran synthase," *PNAS*, 98(15):8915-8920, 2001.

Malakhov et al., Database TREMBL, Accession No. Q55207, Nov. 1996.

Mandel et al., "CLA1, a novel gene required for chloroplast development, is highly conserved in evolution," *The Plant Journal*, 9(5):649-658, 1996.

Marshall et al., "Biosynthesis of tocopherols: A re-examination of the biosynthesis and metabolism of 2-methyl-6-phytyl-1,4-benzoquinol," *Phytochemistry*, 24(8):1705-1711, 1985.

McConnell et al., "Role of phabulosa and phavoluta in determining radial patterning in shoots," *Nature*, 411(6838):709-713, 2001.

Misawa et al., "Elucidation of the *Erwinia uredovora* carotenoid biosynthetic pathway by functional analysis of gene products expressed in *Escherichia coli*," *Journal of Bacteriology*, 172(12):6704-6712, 1990.

Misawa et al., "Expression of an *Erwinia phyloene* desaturase gene not only confers multiple resistance to herbicides interfering with carotenoid biosynthesis but also alters xanthophyll metabolism in transgenic plants," *The Plant Journal*, 6(4):481-489, 1994.

Misawa et al., "Functional expression of the *Erwinia uredovora* carotenoid biosynthesis gene crtI in transgenic plants showing an increase of β-carotene biosynthesis activity and resistance to the bleaching herbicide norflurazon," *The Plant Journal*, 4(5):833-840, 1993.

Misawa et al., "Structure and functional analysis of a marine bacterial carotenoid biosynthesis gene cluster and astaxanthin biosynthetic pathway proposed at the gene level," *Journal of Bacteriology*, 177(22):6575-6584, 1995.

Murata et al., EMBL Sequence Database Accession No. D13960, Mar. 1996.

Nakamura et al., "Structural analysis of *Arabidopsis thaliana* chromosome 5. III. sequence features of the regions of 1,191,918 bp covered by seventeen physically assigned P1 clones," *DNA Research*, 4(6):401-414, 1997.

Nakamura et al., Database EMBL, Accession No. AB005246, Jul. 1997.

Nakamura et al., Database EMBL, Accession No. AB009053, Abstract, Dec. 1997, 1998, 2000.

Nawrath et al., "Targeting of the polyhydroxybutyrate biosynthetic pathway to the plastids of *Arabidopsis thaliana* results in high levels of polymer accumulation," *Proc. Natl. Acad. Sci. USA*, 91:12760-12764, 1994.

Newman et al., Database EMBL, Accession No. AA586087, Abstract, Sep. 1997.

Newman et al., Database EMBL, Accession No. R30625, Aug. 1995.

Newman et al., Database EMBL, Accession No. T44803, Feb. 1995.

Newman et al., Debest ID:1262303, Entrez Report, Accession No. AA586087, Sep. 1997.

Norris et al., "Complementation of the *arabidopsis* pds1 mutation with the gene encoding p-hydroxyphenylpyruvate dioxygenase," *Plant Physiol.*, 117:1317-1323, 1998.

Norris et al., "Genetic dissection of carotenoid synthesis in *arabidopsis* defines plastoquinone as an essential component of phytoene desaturation," *The Plant Cell*, 7:2139-2149, 1995.

Oh et al., "Molecular cloning expression, and functional analysis of a cis-prenyltransferase from *Arabidopsis thaliana*," *The Journal of Biological Chemistry*, 275(24):18482-18488, 2000.

Okada et al., "Five geranylgeranyl diphosphate synthase expressed in different organs are localized into three subcellular compartments in *arabidopsis*," *Plant Physiology*, 122:1045-1056, 2000.

Oommen et al., "The elicitor-inducible alfalfa isoflavone reductase promoter confers different patterns of developmental expression in homologous and heterologous transgenic plants," *The Plant Cell*, 6:1789-1803, 1994.

Oster et al., "The G4 gene of *arabidopsis thaliana* encodes a chlorophyll synthase of etiolated plants," *Bot. Acta*, 110:420-423, 1997.

Oster et al., Database Biosis, Accession No. PREV199800047824, Oct. 1997.

Ouyang et al., Database EMBL, Accession No. AF381248, Jan. 2003.

Peisker et al., "Phytol and the breakdown of chlorophyll in senescent leaves," *J. Plant Physiol.*, 135:428-432, 1989.

Pompliano et al., "Probing lethal metabolic perturbations in plants with chemical inhibition of dehydroquinate synthase," *J. Am. Chem. Soc.*, 111:1866-1871, 1989.

Porfirova et al., "Isolation of an arabidopsis mutant lacking vitamin E and identification of a cyclase essential for all tocopherol biosynthesis," *PNAS*, 99(19):12495-12500, 2002.

Querol et al., "Functional analysis of the *Arabidopsis thaliana* GCPE protein involved in plastid isoprenoid biosynthesis," *FEBS Letters*, 514:343-346, 2002.

Rippert et al., "Engineering plant shikimate pathway for production of tocotrienol and improving herbicide resistance," *Plant Physiology*, 134:92-100, 2004.

Rippert et al., "Molecular and biochemical characterization of an *Arabidopsis thaliana* arogenate dehydrogenase with two highly similar and active protein domains," *Plant Mol. Biol.*, 48:361-368, 2002.

Rodriguez-Concepción et al., "1-deoxy-D-xylulose 5-phosphate reductosiomerase and plastid isoprenoid biosynthesis during tomato fruit ripening," *The Plant Journal*, 27(3):213-222, 2001.

Rodriguez-Concepción et al., "Elucidation of the methylerythritol phosphate pathway for isoprenoid biosynthesis in bacteria and plastids. A metabolic milestone achieved through genomics," *Plant Physiology*, 130:1079-1089, 2002.

Rohdich et al., "Cytidine 5'-triphosphate-dependent biosynthesis of isoprenoids: YgbP protein of *Escherichia coli* catalyzes the formation of 4-diphosphocytidyl-2-C-methylerythritol," *Proc. Natl. Acad. Sci. USA*, 96(21):11758-11763, 1999.

Rohmer et al., "Glyceraldehyde 3-phosphate and pyruvate as precursors of isoprenic units in an alternative non-mevalonate pathway for terpenoid biosynthesis," *J. Am. Chem. Soc.*, 118:2564-2566, 1996.

Rohmer et al., "Isoprenoid biosynthesis in bacteria: a novel pathway for the early steps leading to isopentenyl diphosphate," *Biochem. J.*, 295:517-524, 1993.

Rohmer, "A mevalonate-independent route to isopentenyl diphosphate," *Comprehensive Natural Products Chemistry*, 2:45-67, 1999.

Rohmer, "Isoprenoid biosynthesis via the mevalonate-independent route, a novel target for antibacterial drugs?" *Progress in Drug Research*, 50:136-154, 1998.

Romer et al., "Expression of the genes encoding the early carotenoid biosynthetic enzymes in *Capsicum annuum*," *Biochemical and Biophysical Research Communications*, 196(3):1414-1421, 1993.

Rounsley et al., Database EMBL, Accession No. B24116, Oct. 1997.

Rounsley et al., Database EMBL, Accession No. B29398, Oct. 1997.

Rounsley et al., Database TREMBL, Accession No. 064684, Aug. 1998.

Ruzafa et al., "The protein encoded by the *Shewanella colwelliana* melA gene is a p-hydroxyphenylpyruvate dioxygenase," *FEMS Microbiology Letters*, 124:179-184, 1994.

Saint-Guily et al., "Complementary DNA sequence of an adenylate translocator from *Arabidopsis thaliana*," *Plant Physiol.*, 100(2):1069-1071, 1992.

Sandmann et al., "New functional assignment of the carotenogenic genes crtB and crtE with constructs of these genes from erwinia species," *FEMS Microbiology Letters*, 90:253-258, 1992.

Sato et al., "Structural analysis of *Arabidopsis thaliana* chromosome 5. IV. sequence features of the regions of 1,456,315 bp covered by nineteen physically assigned P1 and TAC clones," *DNA Research*, 5:41-54, 1998.

Sato et al., "Structural analysis of *Arabidopsis thaliana* chromosome 5. X. sequence features of the regions of 3,076,755 bp covered by sixty P1 and TAC clones," *DNA Research*, 7(1):31-63, 2000.

Savidge et al., "Isolation and characterization of homogentisate phytyltransferase genes from synechocystis sp. PCC 6803 and *arabidopsis*," *Plant Physiology*, 129:321-332, 2002.

Schwender et al., "*Arabidopsis thaliana* mRNA for partial 1-deoxy-D-xylulose-5-phosphate reductoisomerase (DXR gene)," Entrez Report, Accession No. AJ242588, Aug. 1999.

Schwender et al., "Cloning and heterologous expression of a cDNA encoding 1-deoxy-D-xylulose-5-phosphate reductoisomerase of *Arabidopsis thaliana*," *FEBS Letters*, 455:140-144, 1999.

Scolnik et al., "Nucleotide sequence of an *Arabidopsis* cDNA for geranylgeranyl pyrophosphate synthase," *Plant Physiol.*, 104(4):1469-1470, 1994.

Scolnik et al., Database EMBL, Accession No. L40577, Apr. 1995.

Shewmaker et al., "Seed-specific overexpression of phytoene synthase: increase in carotenoids and other metabolic effects," *The Plant Journal*, 20(4):401-412, 1999.

Shigeoka et al., "Isolation and properties of γ-tocopherol methyltransferase in *Euglena gracilis*," *Biochimica et Biophysica Acta*, 1128:220-226, 1992.

Shintani et al., "Elevating the vitamin E content of plants through metabolic engineering," *Science*, 282:2098-2100, 1998.

Shintani et al., Database NCBI, Accession No. AF104220, Jan. 1999.

Shoemaker et al., Database EMBL, Accession No. AI748688, Jun. 1999.

Shoemaker et al., Database EMBL, Accession No. AI938569, Aug. 1999.

Shoemaker et al., Database EMBL, Accession No. AI988542, Sep. 1999.

Shoemaker et al., Database EMBL, Accession No. AW306617, Jan. 2000.

Singh et al., "Chorismate mutase isoenzymes from sorghum bicolor. Purification and properties," *Archives of Biochemistry and Biophysics*, 243(2):374-384, 1985.

Smith et al., "Antisense RNA inhibition of polygalacturonase gene expresson in transgenic tomatoes," *Nature*, 334:724-726, 1998.

Smith et al., "The challenges of genome sequence annotation or "the devil is in the details," *Nature Biotechnology*, 15:1222-1223, 1997.

Smith et al., "The cloning of two arabidopsis genes belonging to a phosphate transporter family," *Plant Journal*, 11(1):83-92, 1997.

Soll et al., "Hydrogenation of geranylgeraniol," *Plant Physiol.*, 71:849-854, 1983.

Soll et al., "2-methyl-6-phytylquinol and 2, 3-dimethyl-5-phytylquinol as precursors of tocopherol synthesis in spinach chloroplasts," *Phytochemistry*, 19:215-218, 1980.

Soll et al., "Tocopherol and plastoquinone synthase in spinach chloroplasts subfractions," *Arch. Biochem. Biophys.*, 204(2):544-550, 1980.

Sprenger et al., "Identification of a thiamin-dependent synthase in *Escherichia coli* required for the formation of the 1-deoxy-D-xylulose 5-phosphate precursor to isoprenoids, thiamin, and pyridoxol," *Proc. Natl. Acad. Sci. USA*, 94:12857-12862, 1997.

Spurgeon et al., "Biosynthesis of isoprenoid compounds," 1:1-45, 1981.

Stam et al., "The silence of genes in transgenic plants," *Annals of Botany*, 79:3-12, 1997.

Stocker et al., "Identification of the tocopherol-cyclase in the blue-green algae *Anabaena variabilis* KÜTZING (cyanobacteria)," *Helvetica Chimica Acta*, 76:1729-1738, 1993.

Stocker et al., "The substrate specificity of tocopherol cyclase," *Bioorganic & Medicinal Chemistry*, 4(7):1129-1134, 1996.

Sun et al., "Cloning and functional analysis of the β-carotene hydroxylase of *Arabidopsis thaliana*," *The Journal of Biological Chemistry*, 271(40):24349-24352, 1996.

Suzich et al., "3-deoxy-D-arabino-heplulosonate 7-phosphate synthase from carrot root (*Daucus carota*) is a hysteretic enzyme," *Plant Physiol.*, 79:765-770, 1985.

Svab et al., "High-frequency plastid transformation in tobacco by selection for a chimeric aadA gene," *Proc. Natl. Acad. Sci. USA*, 90:913-917, 1993.

Svab et al., "Stable transformation of plastids in higher plants," *Proc. Natl. Acad. Sci., USA*, 87:8526-8530, 1990.

Tabata et al., Database EMBL, Accession No. D64001, Sep. 1995.
Tabata et al., Database EMBL, Accession No. D64006, Sep. 1995.
Tabata et al., Database EMBL, Accession No. D90909, Oct. 1996.
Tabata et al., Database EMBL, Accession No. D90911, Oct. 1996.
Tabata et al., Database EMBL, Accession No. Q55145, Nov. 1996.
Tabata et al., Database EMBL, Accession No. Q55500, Nov. 1996.

Takahashi et al., "A 1-deoxy-D-xylulose-5-phosphate reductoisomerase catalyzing the formation of 2-C-methyl-D-erythritol 4-phosphate in an alternative nonmevalonate pathway for terpenoid biosynthesis," *Proc. Natl. Acad. Sci. USA*, 95:9879-9884, 1998.

Takatsuji, "Zinc-finger transcription factors in plants," *CMLS Cell. Mol. Life Sci.*, Birkhauser Verlag Basel CH, 54(6):582-596, 1998.

Tjaden et al., "Altered plastidic ATP/ADP-transporter activitiy influences potato (*Solanum tubersomum I.*) tuber morphology, yield and composition of tuber starch," *The Plant Journal*, 16(5):531-540, 1998.

Town et al., "Whole genome shotgun sequencing of *Brassica oleracea*, BOGKS71TR BOGK *Brassica oleracea* genomic clone BOGKS71, DNA sequence," Database EMBL Accession No. BH534089, Dec. 2001.

Town et al., "whole genome shotgun sequencing of *Brassica oleracea*, BOGAU46TR BOGA *Brassica oleracea* genomic clone BOGAU46, DNA sequence," Database EMBL Accession No. BH248880, Nov. 2001.

Verwoert et al., "Development specific expression and organelle targeting of the *Escherichia coli* fabD gene, encoding malonyl coenzyme A-acyl carrier protein transacylase in transgenic rape and tobacco seeds," *Plant Molecular Biology*, 26:189-202, 1994.

Walbot, Database EMBL, Accession No. AI795655, Jul. 1999.

Wing et al., Database EMBL, Accession No. AQ690643, Jul. 1999.

Xia et al., "A monofunctional prephenate dehydrogenase created by cleavage of the 5' 109 bp of the tyrA gene from *Erwinia herbicola*," *J. Gen. Microbiol.*, 138(7):1309-1316, 1992.

Xia et al., "The pheA / tyrA / aroF region from *Erwinia herbicola*: an emerging comparative basis for analysis of gene organization and regulation in enteric bacteria," DATABASE Genbank on STN, Accession No. M74133, *J. Mol. Evol.*, 36(2):107-120, Abstract, 1993.

Xia et al., Database EMBL, Accession No. M74133, Jun. 1993.

Yamamoto, "Purification and metal requirements of 3-dehydroquinate synthase for phaseolus mungo seedlings," *Phytochemistry*, 19:779-781, 1980.

Zaka et al., "Changes in carotenoids and tocopherols during maturation of cassia seeds," *Pakistan J. Sci. Ind. Res.*, 30(11):812-814, 1987.

Zeidler et al., "Inhibition of the non-mevalonate 1-deoxy-D-xylulose-5-phosphate pathway of plant isoprenoid biosynthesis by fosmidomycin," *A Journal of Biosciences*, Zeitschrift fuer Naturforschung, Section C, 53(11/12):980-986, 1998.

Zhu et al., "Cloning and functional expression of a novel geranylgeranyl pyrophosphate synthase gene from *Arabidopsis thaliana* in *Escherichia coli*," *Plant Cell Physiol.*, 38(3):357-361, 1997.

Zhu et al., "Geranylgeranyl pyrophosphate synthase encoded by the newly isolated gene GGPS6 from *Arabidopsis thaliana* is localized in mitochondria," *Plant Molecular Biology*, 35:331-341, 1997.

Declaration of Interference, Patent Interference No. 105,300, Martin v. Boronat, May 4, 2005.

Judgment, Patent Interference No. 105,300, Martin v. Boronat, May 27, 2005.

\* cited by examiner

```
At      MMTLNSLSPA  ESKAISFLDT  SRFNPIPKLS  GGFSLRRRNQ  GRGFGKGVKC

At      SVKVQQQQQP  PPAWPGRAVP  EAPRQSWDGP  KPISIVGSTG  SIGTQTLDIV
E col                                    M  KQLTILGSTG  SIGCSTLDVV At      AENPDKFRVV  ALAAGSNVTL  LADQVRRFKP  ALVAVRNESL  INELKEALAD
e col   RHNPEHFRVV  ALVAGKNVTR  MVEQCLEFSP  RYAVMDDEAS  AKLLKTMLQQ At      LDYKLEIIPG  EQGVIEVARH  PEAVTVVTGI  VGCAGLKPTV  AAIEAGKDIA
e col   QGSRTEVLSG  QQAACDMAAL  EDVDQVMAAI  VGAAGLLPTL  AAIRAGKTIL At      LANKETLIAG  GPFVLPLANK  HNVKILPADS  EHSAIFQCIQ  ----------
e col   LANKESLVTC  GRLFMDAVKQ  SKAQLLPVDS  EHNAIFQSLP  QPIQHNLGYA At      GLPEGALRKI  ILTASGGAFR  DWPVEKLKEV  KVADALKHPN  WNMGKKITVD
e col   DLEQNGVVSI  LLTGSGGPFR  ETPLRDLATM  TPDQACRHPN  WSMGRKISVD At      SATLFNKGLE  VIEAHYLFGA  EYDDIEIVIH  PQSIIHSMIE  TQDSSVLAQL
e col   SATMMNKGLE  YIEARWLFNA  SASQMEVLIH  PQSVIHSMVR  YQDGSVLAQL At      GWPDMRLPIL  YTMSWPDRVP  CSEVTWPRLD  LCKLGSLTFK  KPDNVKYPSM
e col   GEPDMRTPIA  HTMAWPNRVN  SGV---KPLD  FCKLSALIFA  APDYDRYPCL At      DLAYAAGRAG  GTMTGVLSAA  NEKAVEMFID  EKISYLDIFK  VVELTCDKHR
e col   KLAMEAFEQG  QAATTALNAA  NEITVAAFLA  QQIRETDIAA  LNLSVLEK--

At      NELVTSPSLE  EIVHYDLWAR  EYAANVQLSS  GARPVHA
e col   MDMREPQCVD  DVLSSVDANA  REVARKEVMR  LAS
```

Figure 1

NUCLEIC ACID SEQUENCES TO PROTEINS INVOLVED IN ISOPRENOID SYNTHESIS

This application is a continuation application of U.S. patent application Ser. No. 09/987,025, filed Nov. 13, 2001, now issued as U.S. Pat. No. 7,067,647, which application is a continuation of U.S. patent application Ser. No. 09/549,787, filed Apr. 14, 2000, now abandoned, which application claims the benefit of the filing date of the provisional Application U.S. Ser. No. 60/129,899, filed Apr. 15, 1999, and the provisional Application, U.S. Ser. No. 60/146,461, filed Jul. 30, 1999.

TECHNICAL FIELD

The present invention is directed to nucleic acid and amino acid sequences and constructs, and methods related thereto.

BACKGROUND

Isoprenoids are ubiquitous compounds found in all living organisms. Plants synthesize a diverse array of greater than 22,000 isoprenoids (Connolly and Hill (1992) *Dictionary of Terpenoids*, Chapman and Hall, New York, N.Y.). In plants, isoprenoids play essential roles in particular cell functions such as production of sterols, contributing to eukaryotic membrane architecture, acyclic polyprenoids found in the side chain of ubiquinone and plastoquinone, growth regulators like abscisic acid, gibberellins, brassinosteroids or the photosynthetic pigments chlorophylls and carotenoids. Although the physiological role of other plant isoprenoids is less evident, like that of the vast array of secondary metabolites, some are known to play key roles mediating the adaptative responses to different environmental challenges. In spite of the remarkable diversity of structure and function, all isoprenoids originate from a single metabolic precursor, isopentenyl diphosphate (IPP) (Wright, (1961) *Annu. Rev. Biochem*. 20:525-548; and Spurgeon and Porter, (1981) in *Biosynthesis of Isoprenoid Compounds*., Porter and Spurgeon eds (John Wiley, New York) Vol. 1, pp 1-46).

A number of unique and interconnected biochemical pathways derived from the isoprenoid pathway leading to secondary metabolites, including tocopherols, exist in chloroplasts of higher plants. Tocopherols not only perform vital functions in plants, but are also important from mammalian nutritional perspectives. In plastids, tocopherols account for up to 40% of the total quinone pool.

Tocopherols and tocotrienols (unsaturated tocopherol derivatives) are well known antioxidants, and play an important role in protecting cells from free radical damage, and in the prevention of many diseases, including cardiac disease, cancer, cataracts, retinopathy, Alzheimer's disease, and neurodegeneration, and have been shown to have beneficial effects on symptoms of arthritis, and in anti-aging. Vitamin E is used in chicken feed for improving the shelf life, appearance, flavor, and oxidative stability of meat, and to transfer tocols from feed to eggs. Vitamin E has been shown to be essential for normal reproduction, improves overall performance, and enhances immunocompetence in livestock animals. Vitamin E supplement in animal feed also imparts oxidative stability to milk products.

The demand for natural tocopherols as supplements has been steadily growing at a rate of 10-20% for the past three years. At present, the demand exceeds the supply for natural tocopherols, which are known to be more biopotent than racemic mixtures of synthetically produced tocopherols. Naturally occurring tocopherols are all d-stereomers, whereas synthetic α-tocopherol is a mixture of eight d,l-α-tocopherol isomers, only one of which (12.5%) is identical to the natural d-α-tocopherol. Natural d-α-tocopherol has the highest vitamin E activity (1.49 IU/mg) when compared to other natural tocopherols or tocotrienols. The synthetic α-tocopherol has a vitamin E activity of 1.1 IU/mg. In 1995, the worldwide market for raw refined tocopherols was $1020 million; synthetic materials comprised 85-88% of the market, the remaining 12-15% being natural materials. The best sources of natural tocopherols and tocotrienols are vegetable oils and grain products. Currently, most of the natural Vitamin E is produced from γ-tocopherol derived from soy oil processing, which is subsequently converted to α-tocopherol by chemical modification (α-tocopherol exhibits the greatest biological activity).

Methods of enhancing the levels of tocopherols and tocotrienols in plants, especially levels of the more desirable compounds that can be used directly, without chemical modification, would be useful to the art as such molecules exhibit better functionality and biovailability.

In addition, methods for the increased production of other isoprenoid derived compounds in a host plant cell is desirable. Furthermore, methods for the production of particular isoprenoid compounds in a host plant cell is also needed.

SUMMARY OF THE INVENTION

The present invention is directed to D-1-deoxyxylulose 5-phosphate reductoisomerase (dxr), and in particular to dxr polynucleotides and polypeptides. The polynucleotides and polypeptides of the present invention include those derived from eukaryotic sources.

Thus, one aspect of the present invention relates to isolated polynucleotide sequences encoding D-1-deoxyxylulose 5-phosphate reductoisomerase proteins. In particular, isolated nucleic acid sequences encoding dxr proteins from plant sources are provided.

Another aspect of the present invention relates to oligonucleotides which include partial or complete dxr encoding sequences.

It is also an aspect of the present invention to provide recombinant DNA constructs which can be used for transcription or transcription and translation (expression) of dxr. In particular, constructs are provided which are capable of transcription or transcription and translation in host cells.

In another aspect of the present invention methods are provided for production of dxr in a host cell or progeny thereof. In particular, host cells are transformed or transfected with a DNA construct which can be used for transcription or transcription and translation of dxr. The recombinant cells which contain dxr are also part of the present invention.

In a further aspect, the present invention relates to methods of using polynucleotide and polypeptide sequences to modify the isoprenoid content of host cells, particularly in host plant cells. Plant cells having such a modified isoprenoid content are also contemplated herein.

The modified plants, seeds and oils obtained by the expression of the dxr are also considered part of the invention.

BRIEF DESCRIPTION OF THE DRAWINGS

FIG. 1 provides an amino acid alignment between the *Arabidopsis* dxr sequence and the *E coli* dxr sequence FIG. 2 provides a schematic diagram of the isoprenoid pathway, both the mevalonate and non-mevalonate pathways.

DETAILED DESCRIPTION OF THE INVENTION

Figure 2:
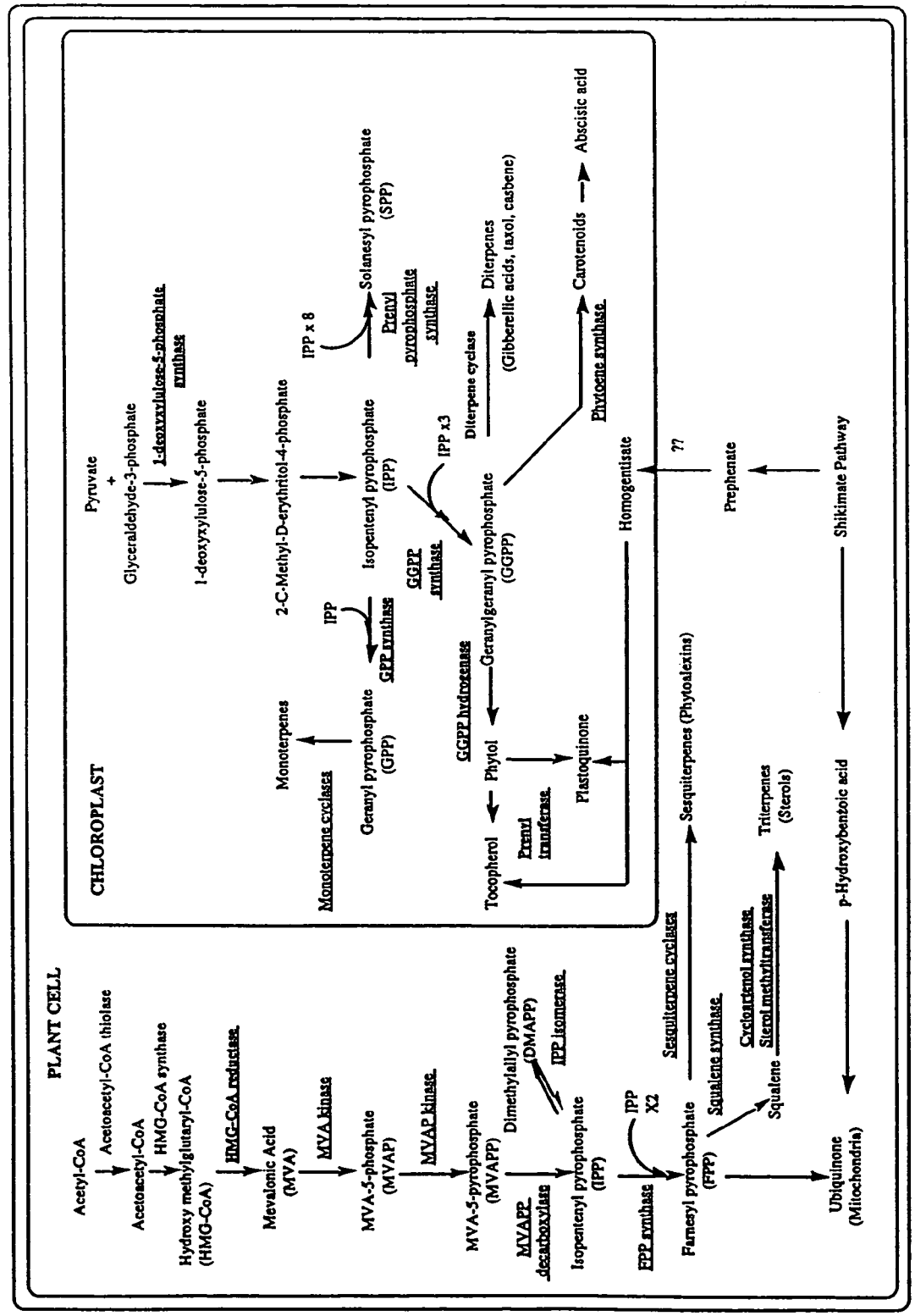

The present invention provides, inter alia, compositions and methods for altering (for example, increasing and decreasing) the isoprenoid levels and/or modulating their ratios in host cells. In particular, the present invention provides polynucleotides, polypeptides, and methods of use thereof for the modulation of isoprenoid content in host plant cells.

Isoprenoids are derived from a 5-carbon building block, isopentenyl diphosphate (IPP), which is the universal isoprene unit and common isoprenoid precursor. Isoprenoids comprise a structurally diverse group of compounds that can be classified into two classes; primary and secondary metabolites (Chappell (1995) *Annu Rev. Plant Physiol. Plant Mol. Biol.* 46:521-547). Primary metabolites comprise those isoprenoids which are necessary for membrane integrity, photoprotection, orchestration of developmental programs, and anchoring biochemical functions to specific membrane systems. Such primary metabolites include, but are not limited to sterols, carotenoids, chlorophyll, growth regulators, and the polyprenol substituents of dolichols, quinones, and proteins. Secondary metabolites mediate important interactions between plants and the environment, but are not necessary to the viability of the plant. Secondary metabolites include, but are not limited to tocopherols, monoterpenes, sesquiterpenes, and diterpenes.

For many years, it was accepted that IPP was synthesized through the well known acetate/mevalonate pathway. However, recent studies have demonstrated the occurrence of an alternative mevalonate-independent pathway for IPP biosynthesis (Horbach et al. (1993) *FEMS Microbiol. Lett.* 111: 135-140; Rohmer et al., (1993) *Biochem J.* 295:517-524). This non-mevalonate pathway for IPP biosynthesis was initially characterized in bacteria and later also in green algae and higher plants (for recent reviews see Lichtenthaler et al. (1997) *Physiol. Plant.* 101:642-652 and Eisenreich et al. (1998) *Chem. Biol.* 5:R221-R233). The first reaction of the novel mevalonate-independent pathway is the condensation of (hydroxyethyl)thiamin derived from pyruvate with the Cl aldehyde group of D-glyceraldehyde 3-phosphate to yield D-1-deoxyxylulose 5-phosphate (Broers (1994) *Ph.D. Thesis* Eidgenossische Technische Hochschule, Zurich, Switzerland; Rohmer et al., (1996) *J. Am. Chem. Soc.* 118:2564-2566). In *Escherichia coli*, D-1-deoxyxylulose (most likely in the form of D-1-deoxyxylulose 5-phosphate) is efficiently incorporated into the prenyl-side chain of menaquinone and ubiquinone (Broers, (1994) supra; Rosa Putra et al., (1998) *Tetrahedron Lett.* 39:23-26). In plants, the incorporation of D-1-deoxyxylulose into isoprenoids has also been reported (Zeidler et al., (1997) *Z Naturforsch* 52c: 15-23, Arigoni et al., (1997) *Proc. Natl. Acad. Sci USA* 94:10600-10605; Sagner et al., (1998) *Chem. Commun.* 2:221-222). In addition, D-1-deoxyxylulose has also been described as a precursor for the biosynthesis of thiamin and pyridoxol. D-1-deoxyxylulose is the precursor molecule of the contiguous five-carbon unit (C4'-C4-C5-C 5'-C5") of thethiazole ring of thiamin in *E. coli* (Therisod et al., (1981) *Biochem. Biophys. Res. Comm.* 98:374-379; David et al. (1981) *J. Am. Chem. Soc.* 103:7341-7342) and in higher plant chloroplasts (Julliard and Douce, (1991) *Proc. Natl. Acad. Sci. USA* 88:2042-2045). The role of D-1-deoxyxylulose in the biosynthesis of pyridoxol in *E. coli* is also well documented (Hill et al., (1989) *J. Am. Chem. Soc.* 111: 1916-1917; Kennedy et al., (1995) *J. Am. Chem. Soc.* 117:1661-1662; Hill etal., (1996) *J. Biol. Chem.* 271:30426-30435). The cloning of genes encoding 1-deoxy-D-xylulose 5-phosphate synthase has recently been reported in bacteria (prenger et al., (1997) *Proc. Natl. Acad. Sci. USA* 94:12957-12962, Lois et al., (1998) *Proc. Natl. Acad. Sci. USA* 95:2105-2110) and plants (Lange et al., (1998) *Proc. Natl. Acad Sci. USA* 95:2100-2104; Bouvier et al., (1998) *Plant Physiol.* 117:1423-1431). FIG. 2 provides a schematic representation of the isoprenoid pathways.

Although the intermediates between 1-deoxy-D-xylulose 5-phosphate and IPP have not yet been characterized, 2-C-methyl-D-erythriyol 4-phosphate has been proposed by Rohmer and co-workers as the first committed precursor for isoprenoid biosynthesis in bacteria (Duvold et al., (1997) *Tetrahedron Lett.* 38:4769-4772; Duvold et al., (1997) *Tetrahedron Lett.* 38:6181-6184). The enzyme 1-deoxy-D-xylulose 5-phosphate reductoisomerase, catalyzing the conversion of 1-D-deoxy-D-xylulose 5-phosphate into 2-C-methyl-D-erythhyol 4-phosphate, has been recently cloned and characterized in *E. coli* (Takahashi et al., (1998) *Proc. Natl. Acad. Sci. USA* 95:99879-9884). The biosynthesis of 2-C-methyl-D-erythitol in plants by an intramolecular rearrangement of 1-deoxy-D-xylulose 5-phosphate has recently been reported by Sagner et al. (1998) *Tetrahedron Lett.* 39:23-26 and Sagner et al. (1998) *Chem. Commun.* 2:221-222.

The present invention provides polynucleotide and polypeptide sequences involved in the production of 2-C-Methyl-D-erythritol-4-phosphate from 1-deoxyxylulose-5-phosphate, referred to as 1-deoxy-D-xylulose 5-phosphate reductoisomerase or dxr. Also provided in the present invention are constructs and methods for the production of altered expression of dxr in host cells, as well as methods for the modification of the isoprenoid pathway, including modification of the biosynthetic flux through the isoprenoid pathway, and for the production of specific classes of isoprenoids in host cells.

Isolated Polynucleotides, Proteins, and Polypeptides

A first aspect of the present invention relates to isolated dxr polynucleotides. The polynucleotide sequences of the present invention include isolated polynucleotides that encode the polypeptides of the invention having a deduced amino acid sequence selected from the group of sequences set forth in the Sequence Listing and to other polynucleotide sequences closely related to such sequences and variants thereof.

The invention provides a polynucleotide sequence identical over its entire length to each coding sequence as set forth in the Sequence Listing. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or prepro-protein sequence. The polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

The invention also includes polynucleotides of the formula:

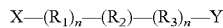

$$X—(R_1)_n—(R_2)—(R_3)_n—Y$$

wherein, at the 5' end X is hydrogen, and at the 3' end, Y is hydrogen or a metal, $R_1$ and $R_3$ are any nucleic acid residue, n is an integer between 1 and 3000, preferably between 1 and 1000 and $R_2$ is a nucleic acid sequence of the invention, particularly a nucleic acid sequence selected from the group set forth in the Sequence Listing and preferably those of SEQ ID NO:1. In the formula, $R_2$ is oriented so that its 5' end residue is at the left, bound to $R_1$, and its 3' end residue is at the right, bound to $R_3$. Any stretch of nucleic acid residues denoted by either R group, where R is greater than 1, may be either a heteropolymer or a homopolymer, preferably a heteropolymer.

The invention also relates to variants of the polynucleotides described herein that encode for variants of the polypeptides of the invention. Variants that are fragments of the polynucleotides of the invention can be used to synthesize full-length polynucleotides of the invention. Preferred embodiments are polynucleotides encoding polypeptide variants wherein 5 to 10, 1 to 5, 1 to 3, 2, 1 or no amino acid residues of a polypeptide sequence of the invention are substituted, added or deleted, in any combination. Particularly preferred are substitutions, additions, and deletions that are silent such that they do not alter the properties or activities of the polynucleotide or polypeptide.

Further preferred embodiments of the invention that are at least 50%, 60%, or 70% identical over their entire length to a polynucleotide encoding a polypeptide of the invention, and polynucleotides that are complementary to such polynucleotides. More preferable are polynucleotides that comprise a region that is at least 80% identical over its entire length to a polynucleotide encoding a polypeptide of the invention and polynucleotides that are complementary thereto. In this regard, polynucleotides at least 90% identical over their entire length are particularly preferred, those at least 95% identical are especially preferred. Further, those with at least 97% identity are highly preferred and those with at least 98% and 99% identity are particularly highly preferred, with those at least 99% being the most highly preferred.

Preferred embodiments are polynucleotides that encode polypeptides that retain substantially the same biological function or activity as the mature polypeptides encoded by the polynucleotides set forth in the Sequence Listing.

The invention further relates to polynucleotides that hybridize to the above-described sequences. In particular, the invention relates to polynucleotides that hybridize under stringent conditions to the above-described polynucleotides. As used herein, the terms "stringent conditions" and "stringent hybridization conditions" mean that hybridization will generally occur if there is at least 95% and preferably at least 97% identity between the sequences. An example of stringent hybridization conditions is overnight incubation at 42° C. in a solution comprising 50% formamide, 5× SSC (150 mM NaCl, 15 mM trisodium citrate), 50 mM sodium phosphate (pH 7.6), 5× Denhardt's solution, 10% dextran sulfate, and 20 micrograms/milliliter denatured, sheared salmon sperm DNA, followed by washing the hybridization support in 0.1×SSC at approximately 65° C. Other hybridization and wash conditions are well known and are exemplified in Sambrook, et al., Molecular Cloning: A Laboratory Manual, Second Edition, cold Spring Harbor, N.Y. (1989), particularly Chapter 11.

The invention also provides a polynucleotide consisting essentially of a polynucleotide sequence obtainable by screening an appropriate library containing the complete gene for a polynucleotide sequence set for in the Sequence Listing under stringent hybridization conditions with a probe having the sequence of said polynucleotide sequence or a fragment thereof; and isolating said polynucleotide sequence. Fragments useful for obtaining such a polynucleotide include, for example, probes and primers as described herein.

As discussed herein regarding polynucleotide assays of the invention, for example, polynucleotides of the invention can be used as a hybridization probe for RNA, cDNA, or genomic DNA to isolate full length cDNAs or genomic clones encoding a polypeptide and to isolate cDNA or genomic clones of other genes that have a high sequence similarity to a polynucleotide set forth in the Sequence Listing. Such probes will generally comprise at least 15 bases. Preferably such probes will have at least 30 bases and can have at least 50 bases. Particularly preferred probes will have between 30 bases and 50 bases, inclusive.

The coding region of each gene that comprises or is comprised by a polynucleotide sequence set forth in the Sequence Listing may be isolated by screening using a DNA sequence provided in the Sequence Listing to synthesize an oligonucleotide probe. A labeled oligonucleotide having a sequence complementary to that of a gene of the invention is then used to screen a library of cDNA; genomic DNA or mRNA to identify members of the library which hybridize to the probe. For example, synthetic oligonucleotides are prepared which correspond to the dxr sequences. The oligonucleotides are used as primers in polymerase chain reaction (PCR) techniques to obtain 5' and 3' terminal sequence of dxr genes. Alternatively, where oligonucleotides of low degeneracy can be prepared from particular dxr peptides, such probes may be used directly to screen gene libraries for dxr gene sequences. In particular, screening of cDNA libraries in phage vectors is useful in such methods due to lower levels of background hybridization.

Typically, a dxr sequence obtainable from the use of nucleic acid probes will show 60-70% sequence identity between the target dxr sequence and the encoding sequence used as a probe. However, lengthy sequences with as little as 50-60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20-50% deviation (i.e., 50-80% sequence homology) from the sequences used as probe. Oligonucleotide probes can be considerably shorter than the entire nucleic acid sequence encoding a dxr enzyme, but should be at least about 10, preferably at least about 15, and more preferably at least about 20 nucleotides. A higher degree of sequence identity is desired when shorter regions are used as opposed to longer regions. It may thus be desirable to identify regions of highly conserved amino acid sequence to design oligonucleotide probes for detecting and recovering other related dxr genes. Shorter probes are often particularly useful for polymerase chain reactions (PCR), especially when highly conserved sequences can be identified. (See, Gould, et al., PNAS USA (1989) 86:1934-1938.).

Another aspect of the present invention relates to dxr polypeptides. Such polypeptides include isolated polypeptides set forth in the Sequence Listing, as well as polypeptides and fragments thereof, particularly those polypeptides which exhibit dxr activity and also those polypeptides which have at least 50%, 60% or 70% identity, preferably at least 80% identity, more preferably at least 90% identity, and most preferably at least 95% identity to a polypeptide sequence selected from the group of sequences set forth in the Sequence Listing, and also include portions of such polypeptides, wherein such portion of the polypeptide preferably includes at least 30 amino acids and more preferably includes at least 50 amino acids.

"Identity", as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" can be readily calculated by known methods including, but not limited to, those described in *Computational Molecular Biology*, Lesk, A. M., ed., Oxford University Press, New York (1988); *Biocomputing: Informatics and Genome Projects*, Smith, D. W., ed., Academic Press, New York, 1993; *Computer Analysis of Sequence Data, Part I*, Griffin, A. M. and Griffin, H. G., eds., Humana Press, New Jersey (1994); *Sequence Analysis in Molecular Biology*, von Heinje, G., Academic Press (1987); *Sequence Analysis Primer*, Gribskov, M. and Devereux, J., eds., Stockton Press, New York (1991); and Carillo, H., and Lipman, D., *SIAM J Applied Math,* 48:1073 (1988). Methods to determine identity are designed to give the largest match between the sequences tested. Moreover, methods to determine identity are codified in publicly available programs. Computer programs which can be used to determine identity between two sequences include, but are not limited to, GCG (Devereux, J., et al., *Nucleic Acids Research* 12(1):387 (1984); suite of five BLAST programs, three designed for nucleotide sequences queries (BLASTN, BLASTX, and TBLASTX) and two designed for protein sequence queries (BLASTP and TBLASTN) (Coulson, *Trends in Biotechnology*, 12: 76-80 (1994); Birren, et al., *Genome Analysis,* 1: 543-559 (1997)). The BLAST X program is publicly available from NCBI and other sources (*BLAST Manual*, Altschul, S., et al., NCBI NLM NIH, Bethesda, Md. 20894; Altschul, S., et al., *J. Mol. Biol.,* 215:403410 (1990)). The well known Smith Waterman algorithm can also be used to determine identity.

Parameters for polypeptide sequence comparison typically include the following:

Algorithm: Needleman and Wunsch, *J. Mol. Biol.* 48:443-453 (1970)

Comparison matrix: BLOSSUM62 from Hentikoff and Hentikoff, *Proc. Natl. Acad. Sci USA* 89:10915-10919 (1992)

Gap Penalty: 12

Gap Length Penalty: 4

A program which can be used with these parameters is publicly available as the "gap" program from Genetics Computer Group, Madison Wis. The above parameters along with no penalty for end gap are the default parameters for peptide comparisons.

Parameters for polynucleotide sequence comparison include the following:

Algorithm: Needleman and Wunsch, *J. Mol. Biol.* 48:443453 (1970)

Comparison matrix: matches=+10; mismatches=0

Gap Penalty: 50

Gap Length Penalty: 3

A program which can be used with these parameters is publicly available as the "gap" program from Genetics Computer Group, Madison Wis. The above parameters are the default parameters for nucleic acid comparisons.

The invention also includes polypeptides of the formula:

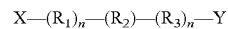

$$X—(R_1)_n—(R_2)—(R_3)_n—Y$$

wherein, at the amino terminus, X is hydrogen, and at the carboxyl terminus, Y is hydrogen or a metal, $R_1$ and $R_3$ are any amino acid residue, n is an integer between 1 and 1000, and $R_2$ is an amino acid sequence of the invention, particularly an amino acid sequence selected from the group set forth in the Sequence Listing and preferably those encoded by the sequences provided in SEQ ID NO:2. In the formula, $R_2$ is oriented so that its amino terminal residue is at the left, bound to $R_1$, and its carboxy terminal residue is at the right, bound to $R_3$. Any stretch of amino acid residues denoted by either R group, where R is greater than 1, may be either a heteropolymer or a homopolymer, preferably a heteropolymer.

Polypeptides of the present invention include isolated polypeptides encoded by a polynucleotide comprising a sequence selected from the group of a sequence contained in the Sequence Listing set forth herein.

The polypeptides of the present invention can be mature protein or can be part of a fusion protein.

Fragments and variants of the polypeptides are also considered to be a part of the invention. A fragment is a variant polypeptide which has an amino acid sequence that is entirely the same as part but not all of the amino acid sequence of the previously described polypeptides. The fragments can be "free-standing" or comprised within a larger polypeptide of which the fragment forms a part or a region, most preferably as a single continuous region. Preferred fragments are biologically active fragments which are those fragments that mediate activities of the polypeptides of the invention, including those with similar activity or improved activity or with a decreased activity. Also included are those fragments that are antigenic or immunogenic in an animal, particularly a human.

Variants of the polypeptide also include polypeptides that vary from the sequences set forth in the Sequence Listing by conservative amino acid substitutions, substitution of a residue by another with like characteristics. In general, such substitutions are among Ala, Val, Leu and Be; between Ser and Thr; between Asp and Glu; between Asn and Gln; between Lys and Arg; or between Phe and Tyr. Particularly preferred are variants in which 5 to 10; 1 to 5; 1 to 3 or one amino acid(s) are substituted, deleted, or added, in any combination.

Variants that are fragments of the polypeptides of the invention can be used to produce the corresponding full length polypeptide by peptide synthesis. Therefore, these variants can be used as intermediates for producing the full-length polypeptides of the invention.

The polynucleotides and polypeptides of the invention can be used, for example, in the transformation of host cells, such as plant host cells, as further discussed herein.

The invention also provides polynucleotides that encode a polypeptide that is a mature protein plus additional amino or carboxyl-terminal amino acids, or amino acids within the mature polypeptide (for example, when the mature form of the protein has more than one polypeptide chain). Such sequences can, for example, play a role in the processing of a protein from a precursor to a mature form, allow protein transport, shorten or lengthen protein half-life, or facilitate manipulation of the protein in assays or production. It is contemplated that cellular enzymes can be used to remove any additional amino acids from the mature protein.

A precursor protein, having the mature form of the polypeptide fused to one or more prosequences may be an inactive form of the polypeptide. The inactive precursors generally are activated when the prosequences are removed. Some or all of the prosequences may be removed prior to activation. Such precursor protein are generally called proproteins.

Constructs and Methods of Use

Of particular interest is the use of the nucleotide sequences in recombinant DNA constructs to direct the transcription or transcription and translation (expression) of the dxr sequences of the present invention in a host cell. The expression constructs generally comprise a promoter functional in a host cell operably linked to a nucleic acid sequence encoding a dxr of the present invention and a transcriptional termination region functional in a host cell. Host cells of particular interest in the present invention include, but are not limited to, fungal cells, yeast cells, bacterial cells, mammalian cells, and plant cells.

A first nucleic acid sequence is "operably linked" or "operably associated" with a second nucleic acid sequence when the sequences are so arranged that the first nucleic acid sequence affects the function of the second nucleic-acid sequence. Preferably, the two sequences are part of a single contiguous nucleic acid molecule and more preferably are adjacent. For example, a promoter is operably linked to a gene if the promoter regulates or mediates transcription of the gene in a cell.

Those skilled in the art will recognize that there are a number of promoters which are functional in plant cells, and have been described in the literature. Chloroplast and plastid specific promoters, chloroplast or plastid functional promoters, and chloroplast or plastid operable promoters are also envisioned.

One set of plant functional promoters are constitutive promoters such as the CaMV35S or FMV35S promoters that yield high levels of expression in most plant organs. Enhanced or duplicated versions of the CaMV35S and FMV35S promoters are useful in the practice of this invention (Odell, et al. (1985) *Nature* 313:810-812; Rogers, U.S. Pat. No. 5,378,619). In addition, it may also be preferred to bring about expression of the dxr gene in specific tissues of the plant, such as leaf, stem, root, tuber, seed, fruit, etc., and the promoter chosen should have the desired tissue and developmental specificity.

Of particular interest is the expression of the nucleic acid sequences of the present invention from transcription initiation regions which are preferentially expressed in a plant seed tissue. Examples of such seed preferential transcription initiation sequences include those sequences derived from sequences encoding plant storage protein genes or from genes involved in fatty acid biosynthesis in oilseeds. Examples of such promoters include the 5' regulatory regions from such genes as napin (Kridl et al., *Seed Sci. Res.* 1:209:219 (1991)), phaseolin, zein, soybean trypsin inhibitor, ACP, stearoyl-ACP desaturase, soybean α' subunit of β-conglycinin (soy 7s, (Chen et al., *Proc. Natl. Acad. Sci.,* 83:8560-8564 (1986))) and oleosin.

It may be advantageous to direct the localization of proteins conferring dxr to a particular subcellular compartment, for example, to the mitochondrion, endoplasmic reticulum, vacuoles, chloroplast or other plastidic compartment. For example, where the genes of interest of the present invention will be targeted to plastids, such as chloroplasts, for expression, the constructs will also employ the use of sequences to direct the gene to the plastid. Such sequences are referred to herein as chloroplast transit peptides (CTP) or plastid transit peptides (PTP). In this manner, where the gene of interest is not directly inserted into the plastid, the expression construct will additionally contain a gene encoding a transit peptide to direct the gene of interest to the plastid. The chloroplast transit peptides may be derived from the gene of interest, or may be derived from a heterologous sequence having a CTP. Such transit peptides are known in the art. See, for example, Von Heijne et al. (1991) *Plant Mol. Biol. Rep.* 9:104-126; Clark et al. (1989) *J. Biol. Chem.* 264:17544-17550; della-Cioppa et al. (1987) *Plant Physiol.* 84:965-968; Romer et al. (1993) *Biochem. Biophys. Res Commun.* 196:1414-1421; and, Shah et al. (1986) *Science* 233:478-481.

Depending upon the intended use, the constructs may contain the nucleic acid sequence which encodes the entire dxr protein, or a portion thereof. For example, where antisense inhibition of a given dxr protein is desired, the entire dxr sequence is not required. Furthermore, where dxr sequences used in constructs are intended for use as probes, it may be advantageous to prepare constructs containing only a particular portion of a dxr encoding sequence, for example a sequence which is discovered to encode a highly conserved dxr region.

The skilled artisan will recognize that there are various methods for the inhibition of expression of endogenous sequences in a host cell. Such methods include, but are not limited to, antisense suppression (Smith, et al. (1988) *Nature* 334:724-726), co-suppression (Napoli, et al. (1989) *Plant Cell* 2:279-289), ribozymes (PCT Publication WO 97/10328), and combinations of sense and antisense Waterhouse, et al. (1998) *Proc. Natl. Acad. Sci. USA* 95:13959-13964. Methods for the suppression of endogenous sequences in a host cell typically employ the transcription or transcription and translation of at least a portion of the sequence to be suppressed. Such sequences may be homologous to coding as well as non-coding regions of the endogenous sequence.

Regulatory transcript termination regions may be provided in plant expression constructs of this invention as well. Transcript termination regions may be provided by the DNA sequence encoding the dxr or a convenient transcription termination region derived from a different gene source, for example, the transcript termination region which is naturally associated with the transcript initiation region. The skilled artisan will recognize that any convenient transcript termination region which is capable of terminating transcription in a plant cell may be employed in the constructs of the present invention.

Alternatively, constructs may be prepared to direct the expression of the dxr sequences directly from the host plant cell plastid. Such constructs and methods are known in the art and are generally described, for example, in Svab, et al. (1990) *Proc. Natl. Acad. Sci. USA* 87:8526-8530 and Svab and Maliga (1993) *Proc. Natl. Acad. Sci. USA* 90:913-917 and in U.S. Pat. No. 5,693,507.

The constructs of the present invention can also be used in methods for altering the flux through the isoprenoid pathway with additional constructs for the expression of additional genes involved in the production of isoprenoids. Such sequences include, but are not limited to 1-deoxyxylulose 5-phosphate synthase.

Furthermore, the constructs of the present invention can be used in transformation methods with additional constructs providing for the expression of additional nucleic acid sequences encoding proteins in the production of specific isoprenoids, such as tocopherols, carotenoids, sterols, monoterpenes, sesquiterpenes, and diterpenes. Nucleic acid sequences involved in the production of carotenoids and methods are described for example in PCT publication WO 99/07867. Nucleic acid sequences involved in the production of tocopherols include, but are not limited to gamma-tocpherol methyltransferase (Shintani, et al. (1998) *Science* 282(5396):2098-2100), tocopherol cyclase, and tocopherol methyltransferase, phytyl prenyltransferase, geranylgeranylpyrophosphate hydrogenase, geranylgeranylpyrophosphate synthase.

A plant cell, tissue, organ, or plant into which the recombinant DNA constructs containing the expression constructs have been introduced is considered transformed, transfected, or transgenic. A transgenic or transformed cell or plant also includes progeny of the cell or plant and progeny produced from a breeding program employing such a transgenic plant as a parent in a cross and exhibiting an altered phenotype resulting from the presence of a dxr nucleic acid sequence.

Plant expression or transcription constructs having a dxr encoding sequence as the DNA sequence of interest for increased or decreased expression thereof may be employed with a wide variety of plant life. Particularly preferred plants for use in the methods of the present invention include, but are not limited to: *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, chicory, cilantro, citrus, clementines, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, mango, melon, mushroom, nectarine, nut, oat, oil palm, oil seed rape, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. Particularly preferred are plants involved in the production of vegetable oils for edible and industrial uses. Most especially preferred are temperate oilseed crops. Temperate oilseed crops of interest include, but are not limited to, rapeseed (Canola and High Erucic Acid varieties), sunflower, safflower, cotton, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

Of particular interest, is the use of dxr constructs in plants to produce plants or plant parts, including, but not limited to leaves, stems, roots, reproductive, and seed, with a modified content of tocopherols in plant parts having transformed plant cells.

For immunological screening, antibodies to the protein can be prepared by injecting rabbits or mice with the purified protein or portion thereof, such methods of preparing antibodies being well known to those in the art. Either monoclonal or polyclonal antibodies can be produced, although typically polyclonal antibodies are more useful for gene isolation. Western analysis may be conducted to determine that a related protein is present in a crude extract of the desired plant species, as determined by cross-reaction with the antibodies to the encoded proteins. When cross-reactivity is observed, genes encoding the related proteins are isolated by screening expression libraries representing the desired plant species. Expression libraries can be constructed in a variety of commercially available vectors, including lambda gt11, as described in Sambrook, et al. (*Molecular Cloning: A Laboratory Manual*, Second Edition (1989) Cold Spring Harbor Laboratory, Cold Spring Harbor, N.Y.).

To confirm the activity and specificity of the proteins encoded by the identified nucleic acid sequences as dxr enzymes, in vitro assays are performed in insect cell cultures using baculovirus expression systems. Such baculovirus expression systems are known in the art and are described by Lee, et al. U.S. Pat. No. 5,348,886, the entirety of which is herein incorporated by reference.

In addition, other expression constructs may be prepared to assay for protein activity utilizing different expression systems. Such expression constructs are transformed into yeast or prokaryotic host and assayed for dxr activity. Such expression systems are known in the art and are readily available through commercial sources.

In addition to the sequences described in the present invention, DNA coding sequences useful in the present invention can be derived from algae, fungi, bacteria, mammalian sources, plants, etc. Homology searches in existing databases using signature sequences corresponding to conserved nucleotide and amino acid sequences of dxr can be employed to isolate equivalent, related genes from other sources such as plants and microorganisms. Searches in EST databases can also be employed. Furthermore, the use of DNA sequences encoding enzymes functionally enzymatically equivalent to those disclosed herein, wherein such DNA sequences are degenerate equivalents of the nucleic acid sequences disclosed herein in accordance with the degeneracy of the genetic code, is also encompassed by the present invention. Demonstration of the functionality of coding sequences identified by any of these methods can be carried out by complementation of mutants of appropriate organisms, such as *Synechocystis, Shewanella*, yeast, *Pseudomonas, Rhodobacteria*, etc., that lack specific biochemical reactions, or that have been mutated. The sequences of the DNA coding regions can be optimized by gene resynthesis, based on codon usage, for maximum expression in particular hosts.

The method of transformation in obtaining such transgenic plants is not critical to the instant invention, and various methods of plant transformation are currently available. Furthermore, as newer methods become available to transform crops, they may also be directly applied hereunder. For example, many plant species naturally susceptible to *Agrobacterium* infection may be successfully transformed via tripartite or binary vector methods of *Agrobacterium* mediated transformation. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation. In addition, techniques of microinjection, DNA particle bombardment, and electroporation have been developed which allow for the transformation of various monocot and dicot plant species.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

Where *Agrobacterium* is used for plant cell transformation, a vector may be used which may be introduced into the *Agrobacterium* host for homologous recombination with T-DNA or the Ti- or Ri-plasmid present in the *Agrobacterium* host. The Ti- or Ri-plasmid containing the T-DNA for recombination may be armed (capable of causing gall formation) or disarmed (incapable of causing gall formation), the latter being permissible, so long as the vir genes are present in the transformed *Agrobacterium* host. The armed plasmid can give a mixture of normal plant cells and gall.

In some instances where *Agrobacterium* is used as the vehicle for transforming host plant cells, the expression or transcription construct bordered by the T-DNA border region(s) will be inserted into a broad host range vector capable of replication in *E. coli* and *Agrobacterium*, there being broad host range vectors described in the literature. Commonly used is pRK2 or derivatives thereof. See, for example, Ditta, et al., (*Proc. Nat. Acad. Sci., U.S.A*. (1980) 77:7347-7351) and EPA 0 120 515, which are incorporated herein by reference. Alternatively, one may insert the sequences to be expressed in plant cells into a vector containing separate replication sequences, one of which stabilizes the vector in *E. coli*, and the other in *Agrobacterium*. See, for example, McBride, et al. (*Plant Mol. Biol.* (1990) 14:269-276), wherein the pRiHRI (Jouanin, et al., *Mol. Gen. Genet.* (1985) 201:370-374) origin of replication is utilized and provides for added stability of the plant expression vectors in host *Agrobacterium* cells.

Included with the expression construct and the T-DNA will be one or more markers, which allow for selection of transformed *Agrobacterium* and transformed plant cells. A number of markers have been developed for use with plant cells, such as resistance to chloramphenicol, kanamycin, the aminoglycoside G418, hygromycin, or the like. The particular marker employed is not essential to this invention, one or another marker being preferred depending on the particular host and the manner of construction.

For transformation of plant cells using *Agrobacterium*, explants may be combined and incubated with the transformed *Agrobacterium* for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

There are several possible ways to obtain the plant cells of this invention which contain multiple expression constructs. Any means for producing a plant comprising a construct having a DNA sequence encoding the expression construct of the present invention, and at least one other construct having another DNA sequence encoding an enzyme are encompassed by the present invention. For example, the expression construct can be used to transform a plant at the same time as the second construct either by inclusion of both expression constructs in a single transformation vector or by using separate vectors, each of which express desired genes. The second construct can be introduced into a plant which has already been transformed with the dxr expression construct, or alternatively, transformed plants, one expressing the dxr construct and one expressing the second construct, can be crossed to bring the constructs together in the same plant.

The nucleic acid sequences of the present invention can be used in constructs to provide for the expression of the sequence in a variety of host cells, both prokaryotic eukaryotic. Host cells of the present invention preferably include monocotyledenous and dicotyledenous plant cells.

In general, the skilled artisan is familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., *Molecular Cloning: A Laboratory Manual*, Cold Spring Harbor Press (1989); Maliga et al., *Methods in Plant Molecular Biology*, Cold Spring Harbor Press (1995), the entirety of which is herein incorporated by reference; Birren et al., *Genome Analysis: Analyzing DNA*, 1, Cold Spring Harbor, N.Y., the entirety of which is herein incorporated by reference).

Methods for the expression of sequences in insect host cells are known in the art. Baculovirus expression vectors are recombinant insect viruses in which the coding sequence for a chosen foreign gene has been inserted behind a baculovirus promoter in place of the viral gene, e.g., polyhedrin (Smith and Summers, U.S. Pat. No., 4,745,051, the entirety of which is incorporated herein by reference). Baculovirus expression vectors are known in the art, and are described for example in Doerfler, *Curr. Top. Microbiol. Immunol.* 131:51-68 (1968); Luckow and Summers, *Bio/Technology* 6:47-55 (1988a); Miller, *Annual Review of Microbiol.* 42:177-199 (1988); Summers, *Curr. Comm. Molecular Biology*, Cold Spring Harbor Press, Cold Spring Harbor, N.Y. (1988); Summers and Smith, *A Manual of Methods for Baculovirus Vectors and Insect Cell Culture Procedures*, Texas Ag. Exper. Station Bulletin No. 1555 (1988), the entireties of which is herein incorporated by reference)

Methods for the expression of a nucleic acid sequence of interest in a fungal host cell are known in the art The fungal host cell may, for example, be a yeast cell or a filamentous fungal cell. Methods for the expression of DNA sequences of interest in yeast cells are generally described in "Guide to yeast genetics and molecular biology", Guthrie and Fink, eds. Methods in enzymology, Academic Press, Inc. Vol 194 (1991) and Gene expression technology", Goeddel ed, Methods in Enzymology, Academic Press, Inc., Vol 185 (1991).

Mammalian cell lines available as hosts for expression are known in the art and include many immortalized cell lines available from the American Type Culture Collection (ATCC, Manassas, Va.), such as HeLa cells, Chinese hamster ovary (CHO) cells, baby hamster kidney (BHK) cells and a number of other cell lines. Suitable promoters for mammalian cells are also known in the art and include, but are not limited to, viral promoters such as that from Simian Virus 40 (SV40) (Fiers et al., *Nature* 273:113 (1978), the entirety of which is herein incorporated by reference), Rous sarcoma virus (RSV), adenovirus (ADV) and bovine papilloma virus (BPV). Mammalian cells may also require terminator sequences and poly-A addition sequences. Enhancer sequences which increase expression may also be included and sequences which promote amplification of the gene may also be desirable (for example methotrexate resistance genes).

Vectors suitable for replication in mammalian cells are well known in the art, and may include viral replicons, or sequences which insure integration of the appropriate sequences encoding epitopes into the host genome. Plasmid vectors that greatly facilitate the construction of recombinant viruses have been described (see, for example, Mackett et al, *J Virol.* 49:857 (1984); Chakrabarti et al., *Mol. Cell. Biol.* 5:3403 (1985); Moss, In: *Gene Transfer Vectors for Mammalian Cells* (Miller and Calos, eds., Cold Spring Harbor Laboratory, N.Y., p. 10, (1987); all of which are herein incorporated by reference in their entirety).

The invention now being generally described, it will be more readily understood by reference to the following examples which are included for purposes of illustration only and are not intended to limit the present invention.

A deposit of the plasmids designated herein as pDXR-At and pBAD-DXR was made with the American Type Culture Collection (ATCC), 10801 University Boulevard, Manassas, Va. 20110-2209 USA on Sep. 27, 2002. The deposits were assigned ATCC Accession Nos. PTA-4727 and PTA-4728, respectively. Access to the deposits will be available during the pendency of the application to the Commissioner of Patents and Trademarks and persons determined by the Commissioner to be entitled thereto upon request. The deposits will be maintained in the ATCC Depository in accordance with 37 C.F.R. §§1.801-1.809. Applicant does not waive any infringement of their rights granted under this patent.

EXAMPLES

Example 1

Synthesis of 2-C-methyl-D-erythritol

2-C-Methyl-D-erythritol with a ca 80% e.e. was synthesized according to a Duvold, et al. (1997) *Tetrahedron Lett* 38:4769-4772 and Duvold, et al. (1997) *Tetrahedron Lett* 38:6181-6184) adapted to the production of larger amounts. A solution of 3-methyl-2(5H)-furanone (200 mg, 2 mmol) in dry ether (20 ml) was added at 0° C. over a period of 15 min to a stirred suspension of $LiAlH_4$ (46 mg, 1.2 mmol) in dry ether (20 ml) under argon. The reaction mixture was stirred at 0° C. for further 2 h. A saturated solution of $NH_4Cl$ (2 ml) was slowly added until the excess of $LiAlH_4$ was destroyed. After acidification with a 1M HCl solution until all aluminum salts were dissolved, the aqueous phase was extracted with ethyl acetate (6×20 ml). The combined organic layers were washed with saturated brine and dried over anhydrous $NaSO_4$. After removal of the solvent under reduced pressure, the crude diol (177 mg) dissolved in methylene chloride (20 ml) was directly acetylated for 15 min with a mixture of acetic anhydride/triethylamine (2:3, v/v, 1 ml) in presence of catalytic amounts of dimethylaminopyridine (12 mg). Solvent and excess or reagents were evaporated under reduced pressure. Flash column chromatography (Still et al., 1978) (hexane/ethyl acetate, 4:1, v/v) afforded pure diacetate (330 mg, 86%). Enantioselective dihydroxylation of diacetate (300 mg, 1.6 mmol) was performed by stirring at 0° C. in terbutanol/water (1:1 v/v, 6 ml) in the presence of the chiral osmylation reagent AD-mix-b (2.5 g) and $CH_3SO_2NH_2$ (152 mg, 1.6 mmol). After 24 hours, the reaction was quenched with solid $Na_2SO_3$ and additional stirring for 30 minutes. Repeated extraction with ethyl acetate (6×20 ml) and flash chromatography (ethyl acetate) afforded a mixture only containing 2-C-methyl-D-erythtol diacetates (resulting from partial intramolecular transesterifications) (312 mg, 88% yield). Quantitative deacetylation was performed overnight at room temperature in the presence of basic Amberlyst A-26 (OH— form) (150 mg for 1 mmol) in methanol (30 ml) (Reed et al., 1981) Filtration of the resin and evaporation of the solvent directly afforded pure 2-C-methyl-D-erythritol (190 mg, 75% overall yield).

Example 2

Site-Directed Marker Insertion Mutagenesis of the dxr Gene of *E. coli*

The region extending from the 5'-region of the dxr gene to the 3'-flanking region of the yaeS gene was amplified by PCR using genomic DNA isolated from the wild type *E. coli* strain-W3110 (Kohara et al., 1987) and the primers P1(5'-CTCTGGATGT CATATGAAGCAACTC-3' (SEQ ID NO:3); the underlined ATG corresponds to the translation start codon of the dxr gene) and P2 (5'-CCGCATAACAC-CGCCAACC-3' (SEQ ID NO:4); located at the 3'-flanking region of the yaeS gene). The reaction mixture for the PCR was prepared in a final volume of 50 µl, containing the DNA template (100 ng), 0.5 µM of each primer, 200 µM of each deoxynucleoside triphosphate, 20 mM of Tris-HCl adjusted to pH 8.8, 2 mM Of $MgSO_4$, 10 mM of KCl, 10 mM of $(NH_4)_2SO_4$, 0.1 mg/ml of BSA and 0.1% Triton X-100. The sample was covered with mineral oil, incubated at 94° C. for 3 min and cooled to 80° C. Pfu DNA polymerase (1.25 units, Stratagene) was added and the reaction mixture was incubated for 30 cycles consisting of 45 sec at 94° C., 45 sec at 59° C. and 10 min at 72° C., followed by a final step of 10 min at 72° C. After amplification, adenines were added to the 3' ends of the PCR product as indicated by the manufacturers protocol and the adenylated product was cloned into the pGEM-T vector (Promega), to create plasmid pMJ1. The CAT (chloramphenicol acetyl transferase) gene present in plasmid pCAT19 (Fuqua, 1992) was excised by digestion with PstI and XbaI, treated with T4 DNA polymerase and cloned into the unique AsuII site present in the dxr gene by blunt end ligation (after treatment with T4 DNA polymerase), resulting plasmid pMJ2. Restriction enzyme mapping was used to identify the clones in which the CAT gene was in the same orientation than the dxr gene. Plasmid pMJ3 was constructed by subcloning the SpeI-SphI fragment excised from plasmid pMJ2 into the NheI-SphI sites of plasmid pBR322. Plasmid pMJ3 was linearized by digestion with PstI, incubated with calf intestinal alkaline phosphatase (GibcoBRL) and purified by agarose gel electrophoresis. Two µg of the purified linear plasmid pMJ3 DNA were used to transform *E coli* strain JC7623 (Winans et al., 1985). Transformed cells were plated onto LB plates (Ausubel et al. 1987) supplemented with 2 mM of 2-C-methyl-D-erythritol (ME) and chloramphenicol (17 µg/mL). Colonies showing both chloramphenicol resistance and ME auxotrophy were selected for further studies. The presence of the CAT gene insertion into the dxr gene was checked by PCR using primers P3 (5'-GCACACTTCCACTGTGTGTG-3' (SEQ ID NO:5), located at the 5'-region of the fir gene) and P2. One of these colonies, designated as strain JC7623dxr:CAT, was used for the complementation studies.

Example 3

Rapid Amplification of cDNA Ends (RACE)

To identify putative plant nucleic acid sequences encoding homologues of the 1-deoxy-D-xylulose 5-phosphate reductoisomerase (DXR), the Non-Redundant database of the National Center for Biotechnology Information (NCBI) was searched with the TBLASTN program, using the complete amino acid sequence of the recently cloned DXR from *Escherichia coli* (Takahashi et al., 1998) as a query. A significant level of identity (40-64%) was found between this query and the amino acid sequence encoded by seven predicted exons of the *A. thaliana* genomic clone MQB2 (Accession number ABOO9053).

To confirm the existence of mRNA sequences corresponding to the putative *A. thaliana* DXR gene, the EST database of the NCBI (dbEST) was searched with the BLASTN program using as a query the nucleotide sequence of clone MOB2 extending from nucleotides 29247 to 31317. Two *A. thaliana* EST clones (12OE8T7 and 65FllXP3', accession numbers T43949 and AA586087, respectively) containing nucleotide sequences identical to different regions of the query were found. Sequencing of the cDNA inserts revealed the two clones were overlapping. The longest cDNA contained an open reading frame encoding a polypeptide of 329 residues showing an identity of 41.6% (similar of 53.2%) with the C-terminal region of the *E. coli* DXR, thus indicating that the two cDNAs encoded truncated versions of the putative *A. thaliana* enzyme.

Total RNA from 12-days-old light-grown *Arabidopsis thaliana* (var. *Columbia*) seedlings was purified as described (Dean et al., 1985). Rapid amplification of cDNA ends (RACE) was carried out with the 5'-RACE-System (Version 2.0) from Life Technologies/Gibco BRL, following the instructions of the supplier. The first strand of cDNA was synthesized using 1 µg of the RNA sample as template and the oligonucleotide DXR-GSP 1 (5'-ATTCGAACCAG-CAGCTAGAG-3' (SEQ ID NO:6), complementary to nucleotides +767 to +786 of the sequence shown in SEQ ID NO:1 as specific downstream primer. After purification and homopolymeric tailing of the cDNA, two nested PCR reactions were performed. In the first PCR, the specific downstream primer was the oligonucleotide DXR-GSP2 (5'-CCAGTAGATCCAACGATAGAG-3' (SEQ ID NO:7), complementary to nucleotides +530 to +550 of the sequence shown in SEQ ID NO:1) and the upstream primer was the oligonucleotide 5'-RACE-AAP (supplied in the kit). In the second PCR, the specific downstream primer was the oligonucleotide DXR-GSP3 (5'-GGCCATGCTGGAGGAG-GTTG-3' (SEQ ID NO:8), complementary to nucleotides +456 to +475 of the sequence shown in SEQ ID NO:1) and the upstream primer was the oligonucleotide AUAP (supplied in the kit). In both PCR reactions the amplification process was initiated by denaturation of the sample (3 min at 94° C.), cooling to 80° C. and addition of Taq DNA polymerase. The reaction mixture of the first PCR was incubated for 15 cycles consisting of 30 sec at 94° C., 30 sec at 55° C. and 1 min at 72° C., followed by a final step of 5 min at 72° C. The sample obtained was diluted one to ten in the reaction mixture of the second PCR and incubated for 30 cycles consisting of 30 sec at 94° C., 30 sec at 61° C. and 1 min at 72° C., with a final step of 5 min at 72° C. The final amplification products were purified by agarose gel electrophoresis, cloned into plasmid pBluescript SK+ and sequenced (SEQ ID NO:1).

Example 4

Cloning of a 1-deoxy-D-xylulose 5-phosphate Reductoisomerase cDNA from *Arabidopsis thaliana*

To define the 5'-region of the putative DXR gene, the corresponding transcription start site was mapped by using the RACE technique. Primers were designed on the basis of the alignment between the DXR from *E. coli* and the amino acid sequence deduced from the *A. thaliana* genomic clone. The deduced amino acid sequence from the *Arabidopsis* dxr nucleic acid sequence (SEQ ID NO:1) is provided in SEQ ID NO:2. The first strand of cDNA was synthesized using RNA from *A. thaliana* seedlings as a template and the oligonucleotide DXR-GSP1 as primer. This oligonucleotide was complementary to the region between positions +767 and +786 of the genomic sequence shown in SEQ ID NO:1. Subsequently, two nested PCR reactions were carried out to ampl4 the 5' end of the mRNA. The downstream specific primers used for the first and second nested PCR reactions were complementary to the regions extending from positions +530 to +550 (primer DXR-GSP2) and +456 to +475 (primer DXR-GSP3), respectively. Four clones corresponding to the major amplification product were sequenced and found to have the same 5'-end, which corresponds to the adenine at position +1 in the genomic sequence shown in SEQ ID NO:1.

A cDNA containing the whole coding sequence of the *Arabidopsis* DXR was amplified by two consecutive PCR reactions from a cDNA library derived from the *A. thaliana* (var. *Columbia*) cell suspension line T87. An aliquot of the library was ethanol-precipitated and resuspended in water. The reaction mixture for the first PCR was prepared in a final volume of 25 µl containing the DNA template (equivalent to $4 \times 10^5$ pfu of cDNA library), 0.5 µM of the upstream primer DXR-34 (5'-CAAGAGTAGTAGTGCGGTTCTCTGG-3' (SEQ ID NO:9), corresponding to nucleotides +34 to +58 of the sequence shown in SEQ ID NO:1), 0.5 µM of the downstream primer DXR-E2 (5'-CAGTTTGGCTTGTTCG-GATCACAG-3' (SEQ ID NO:10), complementary to nucleotides +3146 to +3169 of the sequence shown in SEQ ID NO:1), 200 µM of each deoxynucleoside triphosphate, 20 mM of Tris-HCl adjusted to pH 8.8, 2 mM Of $MgSO_4$, 10 mM of KCl, 10 MM of $(NH_4)_2SO_4$, 0.1 mg/ml of BSA and 0.1% Triton X-100. The sample was covered with mineral oil, incubated at 94° C. for 3 min and cooled to 80° C. Pfu DNA polymerase (1.25 units, Stratagene) was added and the reaction mixture was incubated for 35 cycles consisting of 30 sec at 94° C., 40 sec at 55° C. and 6.5 min at 72° C., followed by a final step of 15 min at 72° C. The reaction mixture was diluted one to ten with water and 5 µl were used as a template for the second PCR that was performed using the same conditions as described for the previous amplification, except that the volume of the reaction mixture was increased to 50 µl and the number of cycles was reduced to 15. The amplification product was purified by agarose gel electrophoresis and cloned into plasmid pbluescript SK+. The resulting plasmid was named pDXR-At.

Thus, a cDNA clone encoding the entire *A. thaliana* DXR was obtained by PCR from a cDNA library using primers DXR-34 and DXR-E2 corresponding to the regions extending from positions +34 to +58 and +3146 to +3169 of the genomic sequence, respectively. The identity of the amplified cDNA was confirmed by DNA sequencing, The alignment of the cDNA and the genomic sequences showed that the *A. thaliana* DXR gene contains 12 exons and 11 introns which extend over a region of 3.2 Kb (SEQ ID NO:1).

The cloned cDNA encodes a protein of 477 amino acid residues with a predicted molecular mass of 52 kDa. The alignment of *A. thaliana* and *E. coli* DXR (FIG. 1) reveals that the plant enzyme has a N-terminal extension of 79 residues with the typical features of plastid transit peptides (von Heijne et al., 1989). The two proteins show an identity of 42.7% (similarity of 54.3%).

Example 5

Expression Construct Preparation

To express the *A. thaliana* DXR in *E. coli*, the region of the DXR cDNA encoding amino acid residues 81 to 477 was amplified by PCR from plasmid pDXR-At and cloned into a modified version of plasmid pBAD-GFPuv (Clontech). In this plasmid, expression is driven by the $P_{BAD}$ promoter which can be induced with arabinose and repressed with glucose. First, plasmid pBAD-GFPuv was modified by removing the NdeI site located between pBR322ori and the araC coding region (position 4926-4931) by site-directed mutagenesis following the method of Kunkel et al. (Kunkel et al., 1987). The oligonucleotide pBAD-mut1 (5'-CTGAGAGTGCACCATCTGCGGTGTGAAATACC-3' (SEQ ID NO:11)) was used as mutagenic primer. The resulting plasmid was designated pBAD-Mi. Next, NdeI and EcoRI restriction sites were introduced at appropriate positions of the *A. thaliana* DXR cDNA by PCR, using the plasmid pDXR-At as template and the oligonucleotides 5'-MVKPI (5'-GGCATATGGTGAAACCCATCTCTATCGTTGGATC-3' (SEQ ID NO:12), complementary to nucleotides +522 to +544 of the sequence shown in SEQ ID NO:1; the underlined sequence contains the NdeI site) and DXR-END(5'-ACGAATTCATTATGCATGAACTGGCCTAGCACC-3' (SEQ ID NO:13), complementary to nucleotides+2997 to +3018 of the sequence shown in SEQ ID NO:1; the underlined sequence contains the EcoRI site) as mutagenic primers. The PCR amplification product was digested with NdeI and EcoRI and cloned into plasmid pBAD-Ml digested with the same restriction enzyme. This resulted in the substitution of the GFPuv coding sequence in plasmid pBAD-Ml by the corresponding coding sequence of the. *A. thaliana* DXR. The resulting plasmid, designated pBAD-DXR, was introduced into strain XL1-Blue. Plasmid pBAD-Ml, encoding GFPuv, was used as a control in the complementation studies.

Example 6

Analysis of the *Arabidopsis thaliana* dxr

The function of the cloned *A. thaliana* DXR has been established by complementation analysis of an *E. coli* strain carrying a disruption in the dxr gene (strain JC7623dxr.:CAT) (see Example 2). This strain requires 2-C-methyl-D-erythritol (ME) for growth. For the complementation studies we used the region of the *A. thaliana* DXR extending from amino acids 81 to 477 of SEQ ID NO:2, which does not include the putative plastid transit peptide. The appropriate cDNA fragment was cloned into a derivative of plasmid pBAD-GFPuv, under the control of the PBAD promoter, and the resulting plasmid (pBAD-DXR) introduced into the JC7623dxr.-CAT strain. Expression from the PBAD promoter is inducible by arabinose and repressed by glucose. Induction with arabinose allows growth of strain JC7623dxr.-CAT harbouring plasmid PBAD-DXR in the absence of ME, whereas no growth was observed in the presence of glucose. Strain JC7623dxr.,:CAT carrying the control plasmid pBAD-Ml does not grow in the presence of arabinose on medium lacking ME. Strain JC7623dxr.-CAT carrying either plasmid PBAD-DXR or pBAD-GFPuv grows on medium containing ME. These results unequivocally demonstrate that the cloned *A. thaliana* cDNA encodes a functional DXR.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. An isolated polynucleotide selected from the group consisting of:
   a) an isolated polynucleotide comprising a nucleotide sequence encoding amino acids 81 to 477 of the polypeptide of SEQ ID NO:2;
   b) an isolated polynucleotide comprising the regions of SEQ ID NO:1 that encode amino acids 81 to 477 of SEQ ID NO:2, which isolated polynucleotide has been deposited as ATCC Accession No. PTA-4728;
   c) an isolated polynucleotide comprising a nucleotide sequence which has at least 95% identity to that of SEQ ID NO:1 over the entire length of SEQ ID NO:1 that encodes amino acids 81 to 477 of SEQ ID NO:2;
   d) an isolated polynucleotide that hybridizes, under stringent conditions, said stringent conditions comprising overnight incubation at 42° C. in a solution comprising 50% formamide, 5×SSC (150 mM NaCl, 15 mM trisodium citrate), 50 mM sodium phosphate (pH 7.6), 5X Denhardt's solution, 10% dextran sulfate and 20 micrograms/milliliter denatured, sheared salmon sperm DNA, followed by washing the hybridization support in 0.1×SSC at approximately 65° C.; to the entire length of SEQ ID NO:1 that encodes amino acids 81 to 477 of SEQ ID NO:2, and which encodes a 1-deoxy-D-xylulose 5-phosphate reductoisomerase; and
   e) an isolated polynucleotide complementary to the polynucleotide sequence of (a), (b), (c), or (d).

2. A DNA construct, comprising; as operably associated components in the 5' to 3' direction of transcription, a promoter functional in a plant cell, a nucleic acid sequence encoding 1-deoxy-D-xylulose 5-phosphate reductoisomerase according to claim 1, and a transcriptional termination sequence.

3. The DNA construct according to claim 2, wherein said nucleic acid sequence is isolated from a eukaryotic source.

4. The DNA construct according to claim 2, wherein said nucleic acid sequence is isolated from a plant source.

5. The DNA construct according to claim 2, wherein said nucleic acid sequence is isolated from *Arabidopsis*.

6. A host cell comprising the construct of claim 2.

7. A host cell according to claim 6, wherein the host cell is a plant cell.

8. A plant comprising a cell according to claim 7.

* * * * *

SEQUENCE LISTING

<160> NUMBER OF SEQ ID NOS: 13

<210> SEQ ID NO 1
<211> LENGTH: 3400
<212> TYPE: DNA
<213> ORGANISM: Arabidopsis sp

<400> SEQUENCE: 1

```
cttgttacta aatgctcagc gaaatcttta aaaaatgaca aaaatctgtt gggtaccatt      60
caaatccaga ttcctttctt atcatcatct ctctctctca cactgtttat ctgattcgtc     120
ttctctgata atcaagagta gtagtgcggt tctctggaaa atattcgatt tttaaaagac     180
tctgatgatg acattaaact cactatctcc agctgaatcc aaagctattt ctttcttgga     240
tacctccagg ttcaatccaa tccctaaact ctcaggtttc ttcttcttcc tctcttcttt     300
```

```
cctcctcctt ggtcaactct cttttcgatt aaagttgcaa acttttcatta gttgtcttag    360
gctcttgtga atttctctat ctaggtaatc tgttatttct tcaattcgat tttttttggt    420
ttgctttagg tcgtagagtt ttaaatttta catctttgga gtgtttcaca ggtgggttta    480
gtttgaggag gaggaatcaa gggagaggtt ttggaaaagg tgttaagtgt tcagtgaaag    540
tgcagcagca acaacaacct cctccagcat ggcctgggag agctgtccct gaggcgcctc    600
gtcaatcttg ggatggacca aaacccatct ctatcgttgg atctactggt tctattggca    660
ctcaggtttt atttcgatta aggcattatt gtgcagttct tgagtatgac cagactttaa    720
gtttgtctta tgaatgacta gactcataga agaatgatat tttttttctta ctgagttatt    780
gttgcatcat tttatcgac aagaacttcc attttgcaga cattggatat tgtggctgag    840
aatcctgaca aattcagagt tgtggctcta gctgctggtt cgaatgttac tctacttgct    900
gatcaggtaa gttggcttca tttgtaaaaa aattagtatt gagtctctcc aatttgtcat    960
tcagaccact tggaattcag tttaattctc agttcagtgg tagtatcata agcaagatag   1020
tattaactcg ttatgtatca gatcaaacca gagaaatcag gttctggttt aggcttttgc   1080
ttctgcaatc tcaagaaatc tctatagtat ggttctgtga ttctattttg aatggtggca   1140
ggtaaggaga tttaagcctg cattggttgc tgttagaaac gagtcactga ttaatgagct   1200
taaagaggct ttagctgatt tggactataa actcgagatt attccaggag agcaaggagt   1260
gattgaggtt agttcatttg ttagttttga ttgtagtgta gataggtttt tacttattat   1320
gttcatcaac aggttgcccg acatcctgaa gctgtaaccg ttgttaccgg aatagtaggt   1380
tgtgcgggac taaaggtata tactctaatt ttttgttatt aaaccttatt aagaggatat   1440
gaaaaaagaa agttgcagat gataaagctt gttgcttatt tttactgcag cctacggttg   1500
ctgcaattga agcaggaaag gacattgctc ttgcaaacaa agagacatta atcgcaggtg   1560
gtcctttcgt gcttccgctt gccaacaaac ataatgtaaa gattcttccg gcagattcag   1620
aacattctgc catatttcag gtatcacaaa tcacatagaa ttaagtacct caactttcat   1680
attgagttca gcgttggtct taatgcaagt tcaacctctg gcaatttgag tgaaaaatct   1740
tcttttatgt tctctagtgt attcaaggtt tgcctgaagg cgctctgcgc aagataatct   1800
tgactgcatc tggtggagct tttaggtttg tttcgatatt cttctctctc tgcatagact   1860
ttttttcttc tcaattctcg tttggttaat ggaaactttt cactggattt tgaaaaaggg   1920
attggcctgt cgaaaagcta aaggaagtta aagtagcgga tgcgttgaag catccaaact   1980
ggaacatggg aaagaaaatc actgtggact ctgctacgct tttcaacaag gttaagatta   2040
ttttctccta aggttaaact ctgattttga aaataccttt gatcaaggta gatgagttct   2100
tgatttttg aaacagggtc ttgaggtcat tgaagcgcat tatttgtttg gagctgagta   2160
tgacgatata gagattgtca ttcatccgca aagtatcata cattccatga ttgaaacaca   2220
ggtcttgctg aaacattact aactaaatta ttatttttcc ggttttaaaa aaataactgt   2280
ataacatgta tttgttttgt tccacaggat tcatctgtgc ttgctcaatt gggttggcct   2340
gatatgcgtt taccgattct ctacaccatg tcatggcccg atagagttcc ttgttctgaa   2400
gtaacttggc caagacttga cctttgcaag taagctaacc acatttatat actctctgtt   2460
tatcaagtgt gaagctaagc ttagttgaaa atttttaatta tcaccaagaa aagttcccca   2520
atcttgtttt cagtttggtt ttaggttgtt tagataagat aaaaaatgaa accgaatcgg   2580
tcttcggttt ggttttgcaa ttggttattt tgctactgtt ttggtgtgga tcagttaaac   2640
```

```
tgggttagga ccactgcctt atctatcagc attcagcacc taaaaccaaa agttgtttac    2700
aattgtggat tttggcagac tcggttcatt gactttcaag aaaccagaca atgtgaaata    2760
cccatccatg gatcttgctt atgctgctgg acgagctgga ggcacaatga ctggagttct    2820
cagcgccgcc aatgagaaag ctgttgaaat gttcattgat gaaaagtaag aattattttt    2880
cagttttgag catctcaatg aagttcttga tacgaatcac aattgtttat attctcactt    2940
ttgtttacag gataagctat ttggatatct tcaaggttgt ggaattaaca tgcgataaac    3000
atcgaaacga gttggtaaca tcaccgtctc ttgaagagat tgttcactat gacttgtggg    3060
cacgtgaata tgccgcgaat gtgcagcttt cttctggtgc taggccagtt catgcatgaa    3120
gaattggttg ttggaagaac ataaggaagc ttctgaggaa atgttgaaag aagattagtg    3180
tagagaatgg ggtactactt aatagcgttt ttggcaagga ttatggattg tgtagctaat    3240
ttatctgtga tccgaacaag ccaaactgat aatttgaaac catttttacc aataaaaccg    3300
agcttaattg tttcacatta tatgattaat tacattcatc taagggttct tgaaaagcct    3360
ctgagcttca tgagtagagt tcgcatctcc tgttgtcgtc                          3400
```

<210> SEQ ID NO 2
<211> LENGTH: 477
<212> TYPE: PRT
<213> ORGANISM: Arabidopsis sp

<400> SEQUENCE: 2

```
Met Met Thr Leu Asn Ser Leu Ser Pro Ala Glu Ser Lys Ala Ile Ser
 1               5                  10                  15

Phe Leu Asp Thr Ser Arg Phe Asn Pro Ile Pro Lys Leu Ser Gly Gly
                20                  25                  30

Phe Ser Leu Arg Arg Arg Asn Gln Gly Arg Gly Phe Gly Lys Gly Val
            35                  40                  45

Lys Cys Ser Val Lys Val Gln Gln Gln Gln Pro Pro Ala Trp
         50                  55                  60

Pro Gly Arg Ala Val Pro Glu Ala Pro Arg Gln Ser Trp Asp Gly Pro
 65                  70                  75                  80

Lys Pro Ile Ser Ile Val Gly Ser Thr Gly Ser Ile Gly Thr Gln Thr
                85                  90                  95

Leu Asp Ile Val Ala Glu Asn Pro Asp Lys Phe Arg Val Val Ala Leu
               100                 105                 110

Ala Ala Gly Ser Asn Val Thr Leu Leu Ala Asp Gln Val Arg Arg Phe
            115                 120                 125

Lys Pro Ala Leu Val Ala Val Arg Asn Glu Ser Leu Ile Asn Glu Leu
        130                 135                 140

Lys Glu Ala Leu Ala Asp Leu Asp Tyr Lys Leu Glu Ile Ile Pro Gly
145                 150                 155                 160

Glu Gln Gly Val Ile Glu Val Ala Arg His Pro Glu Ala Val Thr Val
                165                 170                 175

Val Thr Gly Ile Val Gly Cys Ala Gly Leu Lys Pro Thr Val Ala Ala
            180                 185                 190

Ile Glu Ala Gly Lys Asp Ile Ala Leu Ala Asn Lys Glu Thr Leu Ile
        195                 200                 205

Ala Gly Gly Pro Phe Val Leu Pro Leu Ala Asn Lys His Asn Val Lys
    210                 215                 220

Ile Leu Pro Ala Asp Ser Glu His Ser Ala Ile Phe Gln Cys Ile Gln
225                 230                 235                 240
```

```
Gly Leu Pro Glu Gly Ala Leu Arg Lys Ile Ile Leu Thr Ala Ser Gly
                245                 250                 255

Gly Ala Phe Arg Asp Trp Pro Val Glu Lys Leu Lys Glu Val Lys Val
            260                 265                 270

Ala Asp Ala Leu Lys His Pro Asn Trp Asn Met Gly Lys Lys Ile Thr
        275                 280                 285

Val Asp Ser Ala Thr Leu Phe Asn Lys Gly Leu Glu Val Ile Glu Ala
    290                 295                 300

His Tyr Leu Phe Gly Ala Glu Tyr Asp Asp Ile Glu Ile Val Ile His
305                 310                 315                 320

Pro Gln Ser Ile Ile His Ser Met Ile Glu Thr Gln Asp Ser Ser Val
                325                 330                 335

Leu Ala Gln Leu Gly Trp Pro Asp Met Arg Leu Pro Ile Leu Tyr Thr
            340                 345                 350

Met Ser Trp Pro Asp Arg Val Pro Cys Ser Glu Val Thr Trp Pro Arg
        355                 360                 365

Leu Asp Leu Cys Lys Leu Gly Ser Leu Thr Phe Lys Lys Pro Asp Asn
    370                 375                 380

Val Lys Tyr Pro Ser Met Asp Leu Ala Tyr Ala Ala Gly Arg Ala Gly
385                 390                 395                 400

Gly Thr Met Thr Gly Val Leu Ser Ala Ala Asn Glu Lys Ala Val Glu
                405                 410                 415

Met Phe Ile Asp Glu Lys Ile Ser Tyr Leu Asp Ile Phe Lys Val Val
            420                 425                 430

Glu Leu Thr Cys Asp Lys His Arg Asn Glu Leu Val Thr Ser Pro Ser
        435                 440                 445

Leu Glu Glu Ile Val His Tyr Asp Leu Trp Ala Arg Glu Tyr Ala Ala
    450                 455                 460

Asn Val Gln Leu Ser Ser Gly Ala Arg Pro Val His Ala
465                 470                 475

<210> SEQ ID NO 3
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 3
ctctggatgt catatgaagc aactc                                       25

<210> SEQ ID NO 4
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 4
ccgcataaca ccgccaacc                                              19

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
```

```
gcacacttcc actgtgtgtg                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
attcgaacca gcagctagag                                                    20

<210> SEQ ID NO 7
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 7
ccagtagatc caacgataga g                                                  21

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
ggccatgctg gaggaggttg                                                    20

<210> SEQ ID NO 9
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 9
caagagtagt agtgcggttc tctgg                                              25

<210> SEQ ID NO 10
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 10
cagtttggct tgttcggatc acag                                               24

<210> SEQ ID NO 11
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 11
ctgagagtgc accatctgcg gtgtgaaata cc                                      32

<210> SEQ ID NO 12
<211> LENGTH: 34
<212> TYPE: DNA
<213> ORGANISM: Artificial Sequence
```

```
                                -continued

<220> FEATURE:
<223> OTHER INFORMATION: Synthetic Oligonucleotide

<400> SEQUENCE: 12
ggcatatggt gaaacccatc tctatcgttg gatc                              34

<210> SEQ ID NO 13
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 13
acgaattcat tatgcatgaa ctggcctagc acc                               33
```